(12) United States Patent
George et al.

(10) Patent No.: US 8,470,832 B2
(45) Date of Patent: Jun. 25, 2013

(54) CO-CRYSTALS

(75) Inventors: Neil George, Huddersfield (GB); James Forrest, Huddersfield (GB); Pauline Theresa Gavan, Huddersfield (GB); Rebecca Claire Burton, Huddersfield (GB); Lee Gregory, Huddersfield (GB)

(73) Assignee: Syngenta Limited, Guildford, Surrey (GB)

( * ) Notice: Subject to any disclaimer, the term of this patent is extended or adjusted under 35 U.S.C. 154(b) by 415 days.

(21) Appl. No.: 12/593,339

(22) PCT Filed: Mar. 27, 2008

(86) PCT No.: PCT/GB2008/001066
§ 371 (c)(1),
(2), (4) Date: Feb. 1, 2010

(87) PCT Pub. No.: WO2008/117060
PCT Pub. Date: Oct. 2, 2008

(65) Prior Publication Data
US 2010/0137337 A1  Jun. 3, 2010

(30) Foreign Application Priority Data
Mar. 28, 2007 (GB) .................................. 0706044.5

(51) Int. Cl.
*A01N 43/54* (2006.01)
*A01P 3/00* (2006.01)

(52) U.S. Cl.
USPC ........................................................ 514/256

(58) Field of Classification Search
None
See application file for complete search history.

(56) References Cited

FOREIGN PATENT DOCUMENTS

| DE | EP0310550 | * | 5/1989 |
|----|-----------|---|--------|
| DE | EP 0310550 | * | 5/1989 |
| EP | 0310550 | | 4/1989 |
| EP | 0655441 | | 5/1995 |

OTHER PUBLICATIONS

Sun et al. in Journal of Chemical Thermodynamics 36 (2004) 895-899.*
Sun et al. in Journal of Chemical Thermodynamics 36, 895-899 (2004).*
The Pesticide Manual, Tenth Edition, Editor: Clive Tomlin (1994).*
Childs et al. Molecular Pharmaceutics (4)3, 323-338 (2007).*
Mohamed et al. in Crystal Growth and Design 9(6), 2881-2889 (2009).*
Trask, A.V. in Molecular Pharmaceutics 4(3) 301-309 (2007).*
Childs et al. in the Journal of the American Chemical Society 126, 13335-13342 (2004).*
Remenar et al. in the Journal of the American Chemical Society 125, 8456-8457 (2003).*
McNamara et al. in Pharmaceutical Research, 23(8), 1888-1897 (2006).*
Walsh et al Chemical Communications 2003, 186-187.*
Tomlin: "The Pesticide Manual, 10th ed." 1994, British Crop Protection Council & The Royal Society of Chemistry, pp. 161-162.
Sun et al.: "Heat Capacity and Enthalpy of Fusion of Pyrimethanil Laurate" Journal of Chemical Thermodynamics, Academic Press, London, GB, vol. 36, No. 10, Oct. 2004, pp. 895-899.
Bond: "What is a Co-Crystal?" Cryst Eng Comm, Royal Society of Chemistry, Cambridge, GB, vol. 9, Jul. 11, 2007, pp. 833-834.
Childs et al.: "The Salt-Cocrystal Continuum: The Influence of Crystal Structure on Ionization State" Molecular Pharmaceutics, vol. 4, No. 3, Apr. 27, 2007, pp. 323-338.
Stahly: "Diversity in Single- and Multiple-Component Crystals. The Search for and Prevalence of Polymorphs and Cocrystals" Cryst. Growth Design, vol. 7, No. 6, May 18, 2007, pp. 1007-1026.

* cited by examiner

*Primary Examiner* — Dennis Heyer
(74) *Attorney, Agent, or Firm* — R. Kody Jones

(57) ABSTRACT

The present invention relates to co-crystals of cyprodinil or pyrimethanil and a co-crystal forming compound which has at least one organic acid functional group. In particular, the present invention relates to co-crystals of cyprodinil and benzoic acid, succinic acid, fumaric acid, maleic acid, oxalic acid, pyrazine carboxylic acid, glycolic acid, levulinic acid, (2-methylphenoxy)acetic acid, hexanedioic acid, 4-(methylamino) benzoic acid, trimethyl acetic acid, pyruvic acid or 4-hydroxy-4'-biphenyl carboxylic acid.

6 Claims, 24 Drawing Sheets

CO-CRYSTALS

This application is a 371 of International Application No. PCT/GB2008/001066 filed Mar. 27, 2008, which claims priority to GB 0706044.5 filed Mar. 28, 2007, the contents of which are incorporated herein by reference.

The present invention relates to novel co-crystals of cyprodinil and pyrimethanil and their use in fungicidal compositions, in particular agrochemical compositions.

Both cyprodinil and pyrimethanil are anilinopyrimidine fungicides and are thought to act by inhibiting the biosynthesis of methionine and the secretion of fungal hydrolytic enzymes. Cyprodinil is used as a foliar fungicide on cereals, grapes, pome fruit, stone fruit, strawberries, vegetables, field crops and ornamentals and as a seed dressing on barley to control a wide range of pathogens such as *Tapesia yallundae* and *T. acuformis, Erysiphe* spp., *Pyrenophora teres, Rhynchosporium secalis, Botrytis* spp., *Alternaria* spp., *Venturia* spp. and *Monilinia* spp. Pyrimethanil is used to control grey mould (*Botrytis cinerea*) on vines, fruit, vegetables and ornamentals and in the control of leaf scab (*Venturia inaequalis* or *V. pirina*) on pome fruit. Both are available commercially and are described in "The Pesticide Manual" [The Pesticide Manual—A World Compendium; Thirteenth Edition; Editor: C. D. S. Tomlin; The British Crop Protection Council].

Two polymorphic forms of cyprodinil are known to exist, both of which exhibit characteristic, but different, melting ranges: form A exhibits between 70 and 72° C. and form B between 74 and 76° C. The thermodynamic stability of polymorphic forms A and B is enantiotropically related and exhibits a phase transition temperature, which, although sensitive to other conditions, is typically at between 15 and 40° C.—certainly within the range of temperature fluctuations that may occur during the processing and storage of agrochemical formulations (typically −10° C. and +50° C.). Below the phase transition temperature form A is the thermodynamically stable form and above, form B is the thermodynamically stable form. Therefore, under storage conditions a solid state of cyprodinil may undergo transformation by recrystallisation between the two polymorphic forms leading to the generation of large and undesirable particles, which could, for example, block spray nozzles during application of the product. In addition, such recrystallisation events mean that it may be difficult to maintain the product as a homogeneous formulation and this may lead to issues during transfer to dilution tanks and in ensuring the correct concentration on dilution. Accordingly, this behaviour currently limits the formulation of cyprodinil to formats in which cyprodinil is solubilised e.g. emulsion concentrates. Similar issues exist with pyrimethanil, which may also crystallise under normal formulation and storage conditions. In addition, pyrimethanil is a rather volatile compound. These issues make formulation as, for example, a suspension concentrate difficult and restrict the use or pyrimethanil in certain situations. As such, therefore, these issues mean that problems similar to those seen with cyprodinil occur during formulation, storage and application of pyrimethanil.

The formation of new solid states of cyprodinil and pyrimethanil which do not exhibit phase transformation within the storage temperature fluctuation window and/or which do not undergo crystallisation on formulation and storage and/or which are less volatile, would enable formulation as solid dispersions (i.e. suspension concentrates, suspoemulsions and wet granulations) which may have desirable toxicology, controlled release or chemical stability properties.

Accordingly, the present invention provides novel co-crystalline forms of cyprodinil or pyrimethanil with improved properties as compared to the commercially available versions of this fungicide.

In particular, the invention provides a co-crystal of cyprodinil or pyrimethanil with a co-crystal forming compound which has at least one organic acid functional group. More suitably, the invention provides a co-crystal of cyprodinil with a co-crystal forming compound which has at least one organic acid functional group. Suitably, the organic acid contains at least one sulphonic acid or carboxylic acid functional group.

Suitable co-crystal forming compounds containing at least one sulphonic acid functional group include, but are not limited to 1,5-napthalene-disulphonic acid, 1,2-naphthalene-disulfonic acid, 4-chlorobenzene sulphonic acid, benzenesulphonic acid, cyclamic acid, methanesulphonic acid and p-toluene sulphonic acid.

Suitable co-crystal forming compounds containing at least one carboxylic acid functional group include, but are not limited to, 1-hydroxy-2-naphthoic acid, 4-aminobenzoic acid, acetic acid, trimethylacetic acid, (2-methylphenoxy) acetic acid, adipic acid, alanine, arginine, ascorbic acid, asparagine, aspartic acid, azelaic acid, benzenesulphonic acid, benzoic acid, 4-methylaminobenzoic acid, 2-phenoxybenzoic acid, 2-acetoxybenzoic acid, camphoric acid, capric acid, cinnamic acid, citric acid, cysteine, dimethylglycine, formic acid, fumaric acid, galactaric acid, gentisic acid, gluconic acid, glucaronic acid, glutamic acid, glutamine, glutaric acid, glycine, glycolic acid, hexanedioic acid, hippuric acid, histidine, isoleucine, lactic acid, lactobionic acid, lauric acid, leucine, levulinic acid, lysine, maleic acid, malic acid, malonic acid, mandelic acid, methionine, nicotinic acid, orotic acid, oxalic acid, palmitic acid, pamoic acid, phenylalanine, pimelic acid, proline, propionic acid, pyroglutamic acid, pyrazine carboxylic acid, pyruvic acid, 4-amino salicyclic acid, salicyclic acid, sebacic acid, serine, stearic acid, suberic acid, succinic acid, tartaric acid, thiocyanic acid, threonine, trichloroacetic acid, trifluoroacetic acid, tryptophan, tyrosine, valine, biphenyl-4-carboxylic acid, biphenyl-2-carboxylic acid, 4'-methyl-2-biphenylcarboxylic acid, 4-biphenylacetic acid, 4'-hydroxy-4-biphenylcarboxylic acid and fenbufen. Suitable co-crystal forming compounds containing two carboxylic acid functional groups include, but are not limited to adipic acid, aspartic acid, azelaic acid, camphoric acid, fumaric acid, glutamic acid, glutaric acid, maleic acid, malic acid, malonic acid, oxalic acid, pimelic acid, sebacic acid, suberic acid, succinic acid and tartaric acid More suitably, the co-crystal forming compound is benzoic acid, succinic acid, fumaric acid, maleic acid, oxalic acid, pyrazine carboxylic acid, glycolic acid, levulinic acid, (2-methylphenoxy)acetic acid, hexanedioic acid, 4-(methylamino) benzoic acid, trimethyl acetic acid, pyruvic acid, glycolic acid or 4-hydroxy-4'-biphenyl carboxylic acid. Most suitably, the co-crystal forming compound is benzoic acid or succinic acid, especially succinic acid.

The co-crystalline form of cyprodinil or pyrimethanil and the crystal forming compound may be characterised by a crystal morphology or by selected peaks of the powder X-ray diffraction pattern expressed in terms of 2 theta angles.

In one embodiment of the invention, there is provided a co-crystal form of cyprodinil and benzoic acid which is characterised by a powder X-ray diffraction pattern expressed in terms of 2 theta angles, wherein the powder X-ray diffraction pattern comprise the 2 theta angle values listed in Table 1 or Table 2. These tables show the 2 theta values, d spacings, and relative intensity of selected peak positions of the powder X-ray diffraction pattern of two cyprodinil-benzoic acid co-crystals, the first of which is in the form of white needle crystals, the second in the form of white rhombic crystals.

TABLE 1

| 2θ (°) | d spacing (Å) | Relative Intensity (%) |
| --- | --- | --- |
| 9.034 | 9.780 | 43.9 |
| 10.266 | 8.610 | 64.4 |
| 11.234 | 7.870 | 64.7 |
| 13.704 | 6.456 | 46.2 |
| 17.081 | 5.187 | 42.1 |
| 17.962 | 4.934 | 100.0 |
| 21.717 | 4.089 | 50.1 |
| 23.436 | 3.793 | 47.1 |
| 24.888 | 3.575 | 66.1 |
| 28.476 | 3.132 | 43.7 |

TABLE 2

| 2θ (°) | d spacing (Å) | Relative Intensity (%) |
| --- | --- | --- |
| 11.201 | 7.893 | 56.7 |
| 11.660 | 7.584 | 64.4 |
| 13.978 | 6.331 | 55.9 |
| 15.050 | 5.882 | 52.2 |
| 18.584 | 4.771 | 59.2 |
| 19.297 | 4.596 | 58.3 |
| 20.793 | 4.269 | 58.2 |
| 23.865 | 3.726 | 100.0 |
| 25.697 | 3.464 | 60.9 |
| 26.765 | 3.328 | 56.6 |

It has surprisingly been found that when cyprodinil and an organic acid, in particular, benzoic acid, succinic acid, fumaric acid, maleic acid, oxalic acid or pyrazine carboxylic acid, are allowed to form co-crystals, the resulting co-crystals give rise to improved properties of the cyprodinil as compared to cyprodinil in free form. In particular, the co-crystals do not exhibit the same phase transition that cyprodinil alone exhibits. This is clearly important as it has benefits during manufacturing, formulation and storage. In particular, it is postulated that this new solid state of cyprodinil, will not undergo recrystallisation events during its formulation or storage of both the technical grade material and the formulated material—the technical material and the formulation will therefore retain their homogeneity. In addition, this stable form of cyprodinil will allow new solid formulation formats, such as suspension concentrates, suspo-emulsions and wet granulations, to be developed and will lead to potential purity benefits (due to the ability to isolate the solid state rather than a liquid) as well as improved handling characteristics (e.g. reduced toxicity).

Figure 1:
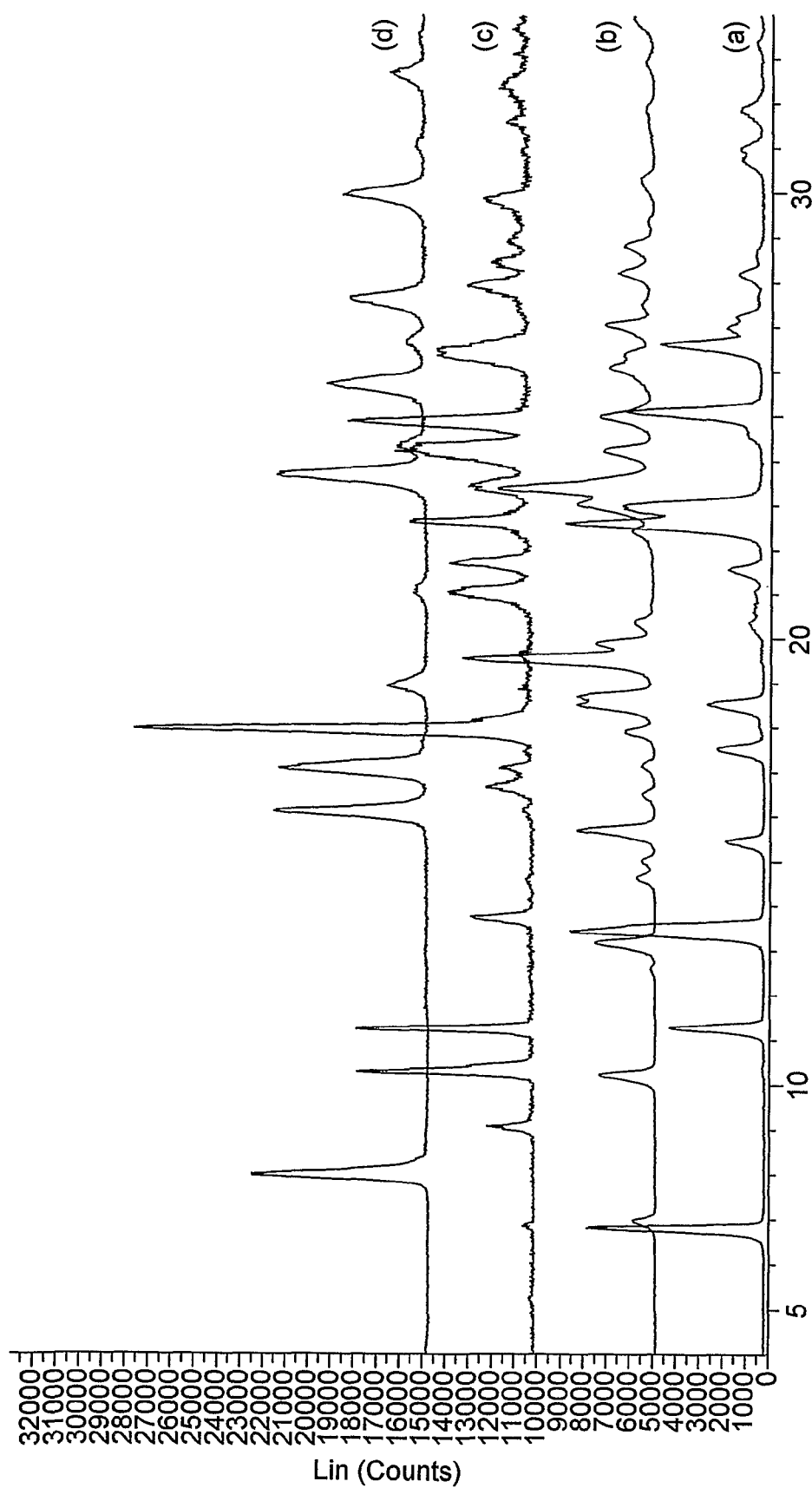
FIG. 1 shows the powder X-Ray diffraction patterns of (a) cyprodinil form A, (b) cyprodinil form B, (c) cyprodinil-benzoic acid crystals (white needle crystals) and (d) benzoic acid.

As used herein 'co-crystal' means a crystalline material which comprises two or more unique components in a stoichiometric ratio each containing distinctive physical characteristics such as structure, melting point and heat of fusion. The co-crystal can be constructed through several modes of molecular recognition including hydrogen-bonding, Π (pi)-stacking, guest-host complexation and Van-Der-Waals interactions. Of the interactions listed above, hydrogen-bonding is the dominant interaction in the formation of the co-crystal, whereby a non-covalent bond is formed between a hydrogen bond donor of one of the moieties and a hydrogen bond acceptor of the other. Preferred co-crystals of the present invention are those where hydrogen bonding occurs between the co-crystal forming compound and the cyprodinil or pyrimethanil.

It is noted that hydrogen bonding can result in several different intermolecular assemblies and, as such, the co-crystals of the present invention may exist in one or more polymeric forms—as for example, is the case with the cyprodinil-benzoic acid crystals detailed above and in the Examples. A polymorphic co-crystal may contain any molar ratio of cyprodinil or pyrimethanil to co-former, but typically will be in the range of 5:1 to 1:5. In systems where the cyprodinil, pyrimethanil or co-former exhibit isomerism, a polymorphic form may also contain a different isomeric ratio. Each polymorphic form can be defined by one or more solid state analytical techniques including single crystal X-ray diffraction, powder X-ray diffraction, DSC, Raman or Infra-red spectroscopy.

Suitably, the molar ratio of cyprodinil or pyrimethanil to co-crystal forming compound in the co-crystal is in the range of from 5:1 to 1:5. More suitably, the ratio of cyprodinil or pyrimethanil to co-crystal forming compound in the co-crystal is in the range of from 3:1 to 1:3. Even more suitably, the ratio of cyprodinil or pyrimethanil to co-crystal forming compound is in the range of 2:1 to 1:1. Most suitably, the ratio of cyprodinil or pyrimethanil to co-crystal forming compound in the co-crystal is approximately 1:1.

The co-crystals of the present invention are formed by contacting the cyprodinil or pyrimethanil with the co-crystal forming compound. This may be done by (i) grinding two solids together, (ii) melting one or both components and allowing them to recrystallise, (iii) solubilising the cyprodinil or pyrimethanil and adding the co-crystal forming compound or (iv) solubilising the co-crystal forming compound and adding the cyprodinil or pyrimethanil. It may also be possible to solubilise the cyprodinil or pyrimethanil in the co-crystal forming compound and vice versa. Crystallisation is then allowed to occur under suitable conditions. For example, crystallisation may require alteration of a property of the solutions, such as pH or temperature and may require concentration of solute, usually by removal of the solvent and typically by drying the solution. Solvent removal results in the concentration of cyprodinil or pyrimethanil increasing over time so as to facilitate crystallisation. Once the solid phase comprising any crystals is formed, this may be tested as described herein.

Accordingly, the present invention provides a process for the production of a co-crystal of the invention comprising
(a) grinding, heating or contacting in solution the cyprodinil or pyrimethanil with the co-crystal forming compound, under crystallisation conditions so as to form a solid phase;
(b) isolating co-crystals comprising the cyprodinil or pyrimethanil and the co-crystal forming compound.

Assaying the solid phase for the presence of co-crystals of the cyprodinil or pyrimethanil and the co-crystal forming compound may be carried out by conventional methods known in the art. For example, it is convenient and routine to use powder X-ray diffraction techniques to assess the presence of the co-crystals. This may be effected by comparing the spectra of cyprodinil or pyrimethanil, the co-crystal forming compound and putative co-crystals in order to establish whether or not true co-crystals have been formed. Other techniques used in an analogous fashion, include differential scanning calorimetry (DSC), thermogravimetric analysis (TGA) and Raman spectroscopy. Single crystal X-ray diffraction is especially useful in identifying co-crystal structures.

The co-crystals of the invention may be readily incorporated into fungicidal compositions (including agrochemical compositions) by conventional means. Accordingly, the invention also provides a fungicidal composition comprising a co-crystal of the invention as defined above. In one embodiment, the fungicidal composition is an agrochemical composition.

The agrochemical compositions comprising the co-crystals of the present invention can be used for the control of plant pathogenic fungi on a number of plant species. Accordingly, the invention also provides a method of preventing/controlling fungal infection on plants or plant propagation material comprising treating the plant or plant propagation material with a fungicidally effective amount of an agricultural composition of the invention. By 'plant propagation material' is meant seeds of all kinds (fruit, tubers, bulbs, grains etc), cuttings, cut shoots and the like.

In particular, the agrochemical compositions of the invention can be used to control, for example, *Cochliobolus sativus, Erysiphe* spp. including *E. graminis, Leptosphaeria nodorum, Puccinia* spp., *Pyrenophora teres, Pyrenophora triticirepentis, Rhynchosporium secalis, Septoria* spp, *Mycosphaerella musicola, Mycosphaerella fijiensis* var. *diformis, Sclerotinia homoeocarpa, Rhizoctonia solani, Puccinia* spp., *Rhizoctonia solani, Helminthosporium oryzae,* dirty panicle complex, *Hemileia vastatrix, Cercospora* spp., *Monilinia* spp., *Podosphaera* spp., *Sphaerotheca* spp., *Tranzschelia* spp. and *Helminthosporium* spp., *Tapesia yallundae* and *T. acuformis, Botrytis* spp., *Alternaria* spp. and *Venturia* spp.

The agrochemical compositions of the present invention are suitable for controlling such disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (Festuca L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia Willd*), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

The rate at which the agrochemical composition of the invention is applied will depend upon the particular type of fungus to be controlled, the degree of control required and the timing and method of application and can be readily determined by the person skilled in the art. In general, the compositions of the invention can be applied at an application rate of between 0.005 kilograms/hectare (kg/ha) and about 5.0 kg/ha, based on the total amount of active fungicide in the composition. An application rate of between about 0.1 kg/ha and about 1.5 kg/ha is preferred, with an application rate of between about 0.3 kg/ha and 0.8 kg/ha being especially preferred.

In practice, the agrochemical compositions comprising the co-crystals of the invention are applied as a formulation containing the various adjuvants and carriers known to or used in the industry. They may thus be formulated as granules, as wettable powders, as emulsifiable concentrates, as suspension concentrates (including oil dispersions), as powders or dusts, as flowables, as solutions, as suspensions or emulsions, suspo-emulsions or as controlled release forms such as microcapsules. Suitably, the agrochemical composition of the invention may be formulated as a suspension concentrate, a suspo-emulsion or a wet granulation. These formulations are described in more detail below and may contain as little as about 0.5% to as much as about 95% or more by weight of the active ingredient in the form of the co-crystal. The optimum amount will depend on formulation, application equipment and nature of the plant pathogenic fungi to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Suspension concentrates are formulations in which finely divided solid particles of the active compound are stably suspended. The solid particles may be suspended in an aqueous solution or in an oil (as an oil dispersion). Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from about 0.5% to about 95% of the concentrate.

Granular formulations include both extrudates and relatively coarse particles and may be applied without dilution to the area in which control of plant pathogenic fungi is required or dispersed in a spray tank before application, for example. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations for use without dilution normally contain about 5% to about 25% active ingredients which may include surface-active agents such as heavy aromatic naphthas, kerosene and other petroleum fractions, or vegetable oils; and/or stickers such as dextrins, glue or synthetic resins. When the granules are to be dispersed in a spray tank before application, the active ingredient content may be increased up to 80%.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimeter to 1 centimeter and preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 40% by weight of the formulation.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulphonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaceous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulphates, such as diethanolammonium lauryl sulphate; alkylarylsulphonate salts, such as calcium dodecylbenzenesulphonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; to alkylnaphthalenesulphonate salts, such as sodium dibutylnaphthalenesulphonate; dialkyl esters of sulphosuccinate salts, such as sodium di(2-ethylhexyl) sulphosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

In addition, further, other biocidally active ingredients or compositions may be combined with the agrochemical composition of this invention. For example, the compositions may contain other fungicides, herbicides, insecticides, bactericides, acaricides, nematicides and/or plant growth regulators, in order to broaden the spectrum of activity.

Each of the above formulations can be prepared as a package containing the fungicides together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of powerdusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In to special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the fungal pathogen.

The present invention will now be described by way of the following non-limiting examples and figures.

EXAMPLES

1. Preparation of Cyprodinil Co-crystals with Benzoic Acid 4 g cyprodinil (form B) and 2.4 g of benzoic acid were added to 200 ml of isohexane at 60° C. in a round-bottomed flask; they dissolved instantly and were held with stirring at 60° C. for 30 mins. The solution was cooled at 10° C./hour down to 25° C., and then held at 25° C. overnight. The product (white needle crystals) was isolated by filtration.

4 g cyprodinil (form B) and 2.4 g of benzoic acid were added to 250 ml of isohexane at 60° C. in a round-bottomed flask; they dissolved instantly and were held with stirring at 60° C. for 30 mins. The solution was cooled by removing the heat source and adding cold water to the water bath holding the round-bottomed flask. The product (white rhombic crystals) was isolated by filtration.

FIG. 1 shows the powder X-Ray diffraction patterns of (a) cyprodinil form A, (b) cyprodinil form B, (c) cyprodinil-benzoic acid crystals (white needle crystals) and (d) benzoic acid.

Figure 2:
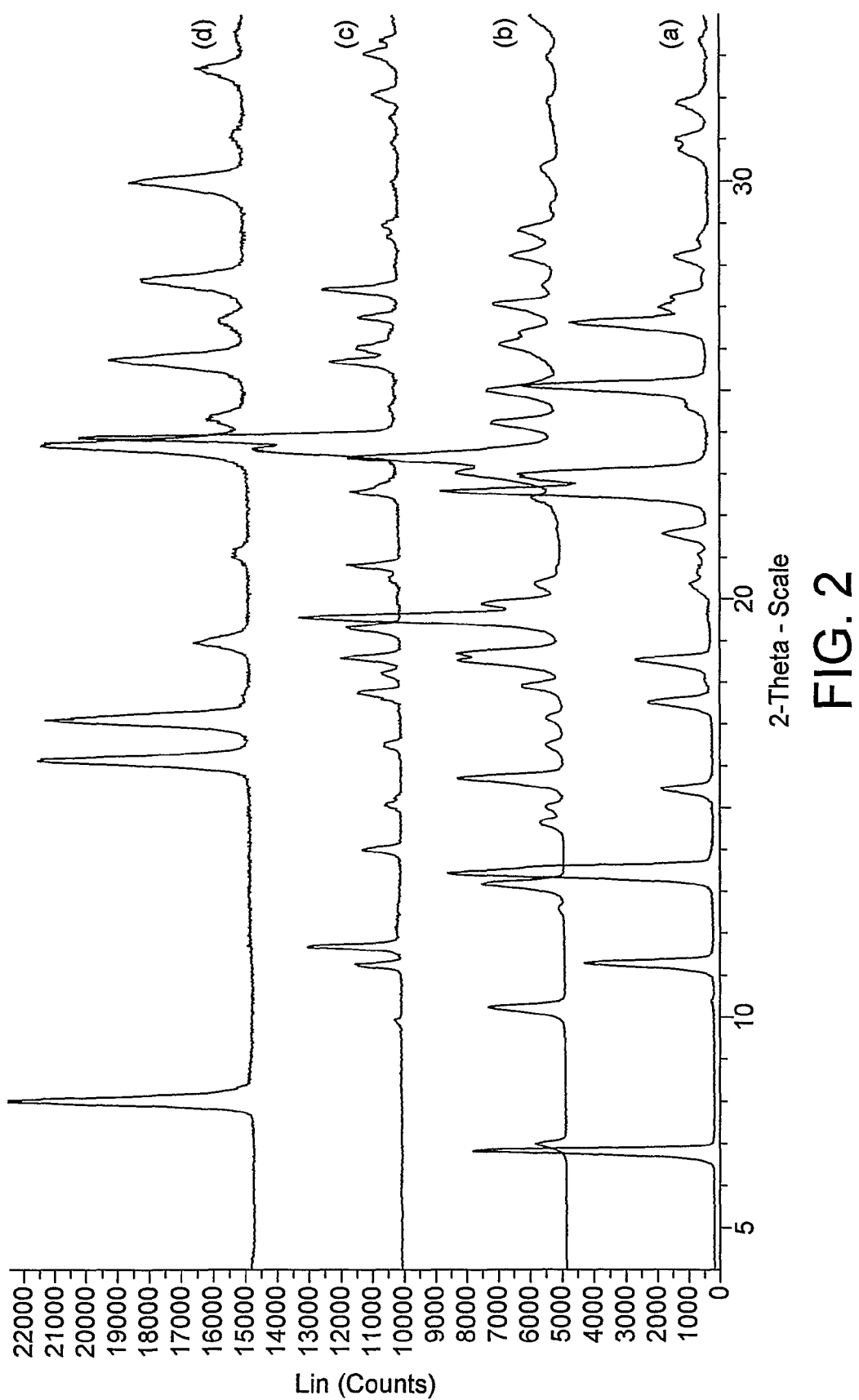
FIG. 2 shows the powder X-Ray diffraction patterns of (a) cyprodinil form A, (b) cyprodinil form B, (c) cyprodinil-benzoic acid crystals (white rhombic crystals) and (d) benzoic acid.

FIG. 2 shows the powder X-Ray diffraction patterns of (a) cyprodinil form A, (b) cyprodinil form B, (c) cyprodinil-benzoic acid crystals (white rhombic crystals) and (d) benzoic acid.

Figure 3:
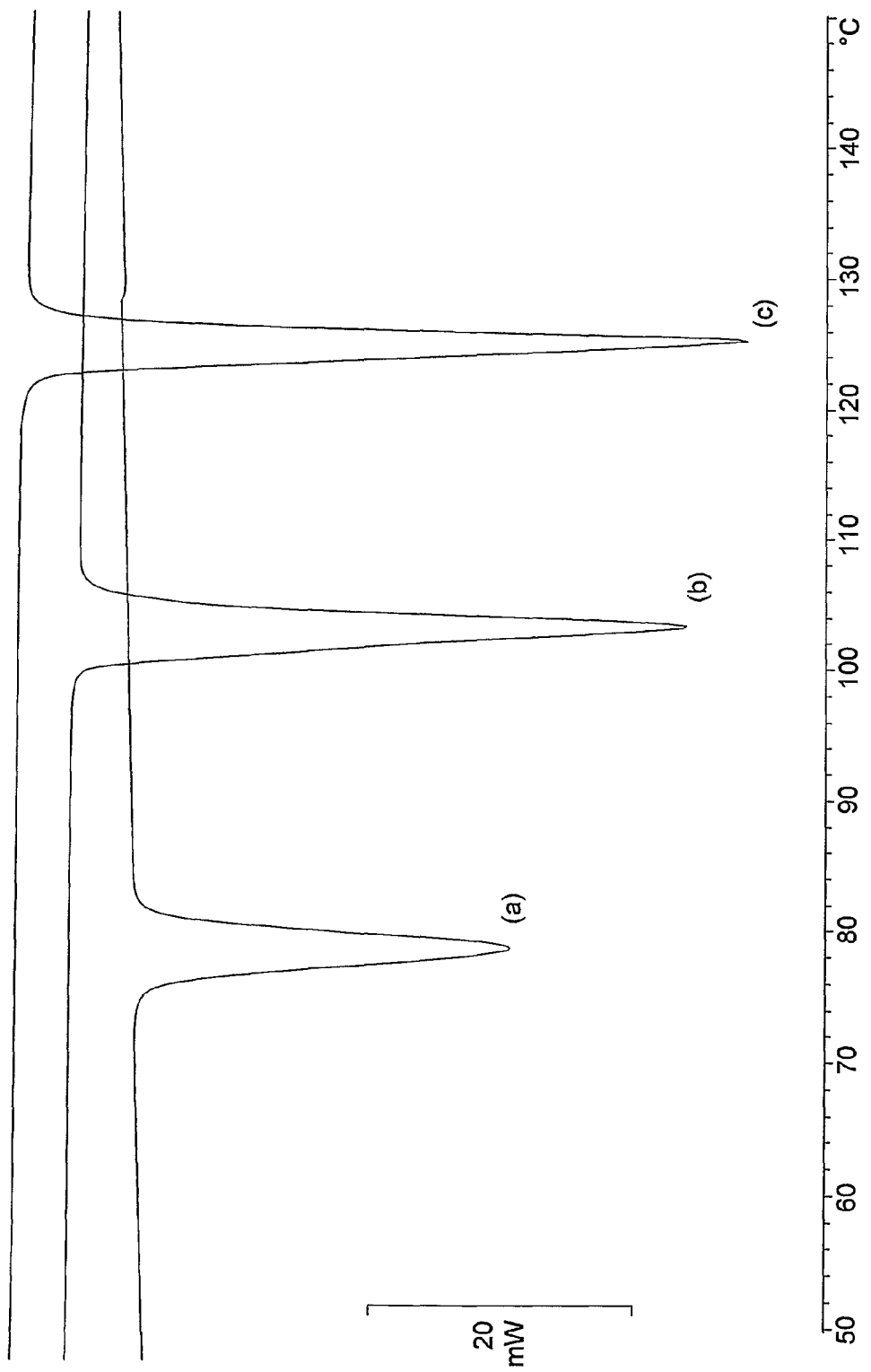
FIG. 3 shows Differential Scanning Calorimetry traces of (a) cyprodinil form B, (b) cyprodinil-benzoic acid crystals (white needle crystals) and (c) benzoic acid.

FIG. 3—shows Differential Scanning Calorimetry traces of (a) cyprodinil form B, (b) cyprodinil-benzoic acid crystals (white needle crystals) and (c) benzoic acid.

Figure 4:
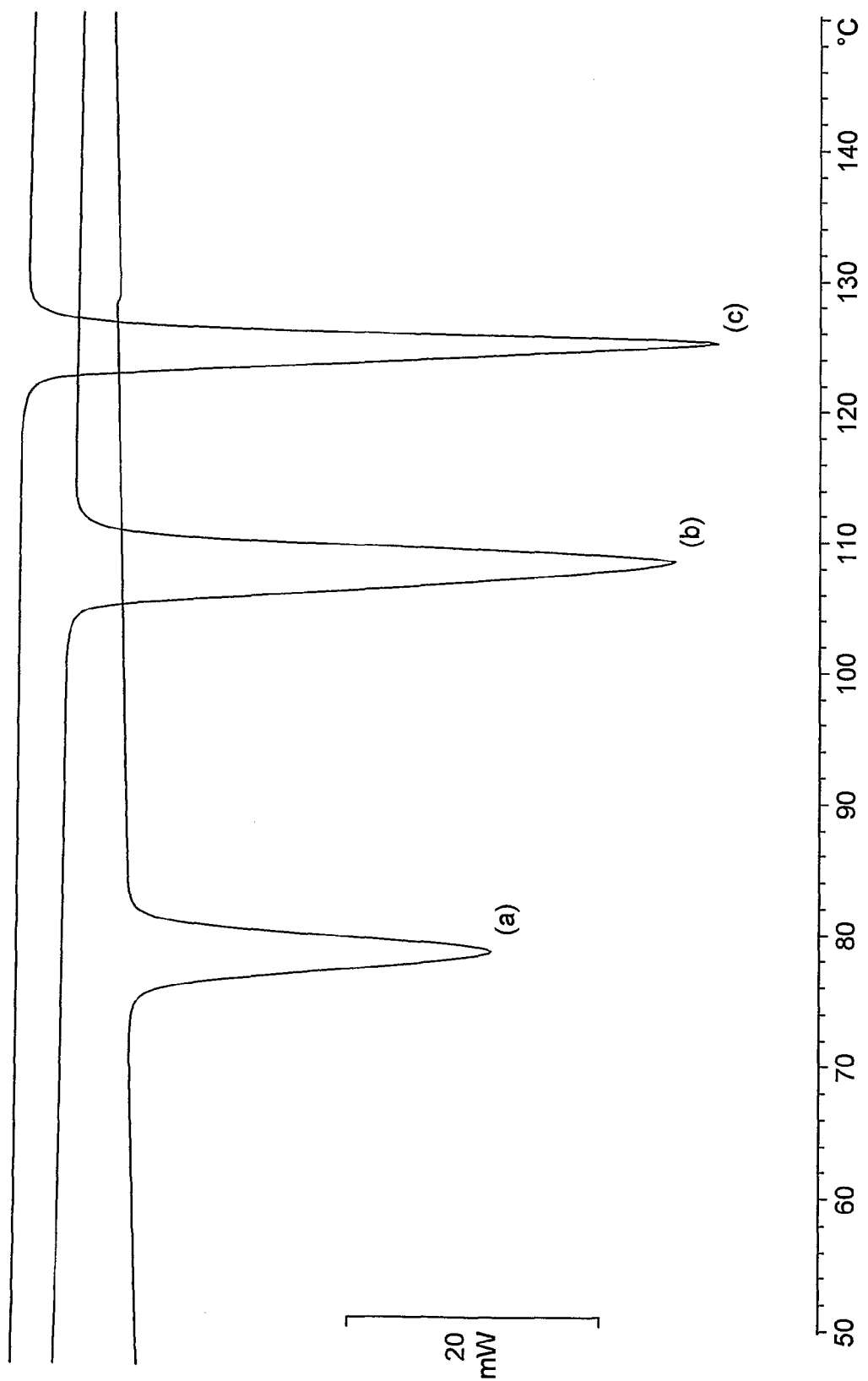
FIG. 4 shows Differential Scanning Calorimetry traces of (a) cyprodinil form B, (b) cyprodinil-benzoic acid crystals (white rhombic crystals) and (c) benzoic acid.

FIG. 4—shows Differential Scanning Calorimetry traces of (a) cyprodinil form B, (b) cyprodinil-benzoic acid crystals (white rhombic crystals) and (c) benzoic acid Powder X-ray diffraction analysis clearly shows that the products bear no resemblance to either of the constituent phases suggesting that a new solid state has been formed.

Differential scanning calorimetry traces of the two products exhibit show that the white needle crystals exhibit a single melting endotherm at 104° C. and the white rhombic crystals at 109° C. The constituent phases melt at 79° C. for cyprodinil form B and 126° C. for benzoic acid.

2. Cyprodinil-Maleic Acid Co-Crystal

Figure 5:
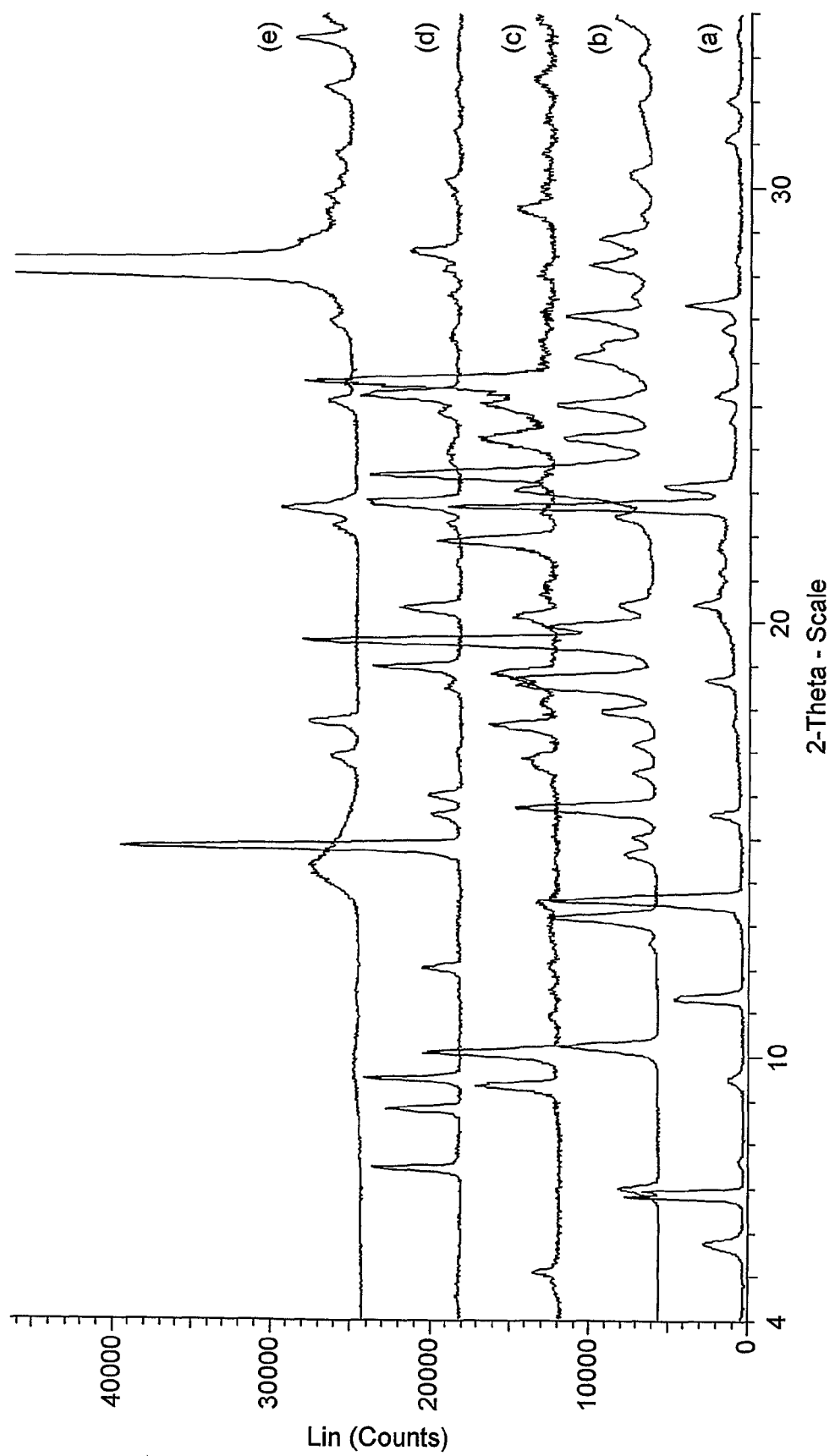
FIG. 5 shows Powder X-Ray Diffraction patterns of Cyprodinil Form A (a), Cyprodinil Form B (b), Cyprodinil-Maleic Acid Co-Crystal Form A (c) and Cyprodinil-Maleic Acid Co-Crystal Form B (d) and Maleic acid (e).

FIG. 5: Powder X-Ray Diffraction patterns of Cyprodinil Form A (a), Cyprodinil Form B (b), Cyprodinil-Maleic Acid Co-Crystal Form A (c) and Cyprodinil-Maleic Acid Co-Crystal Form B (d) and Maleic acid (e).

Figure 6:
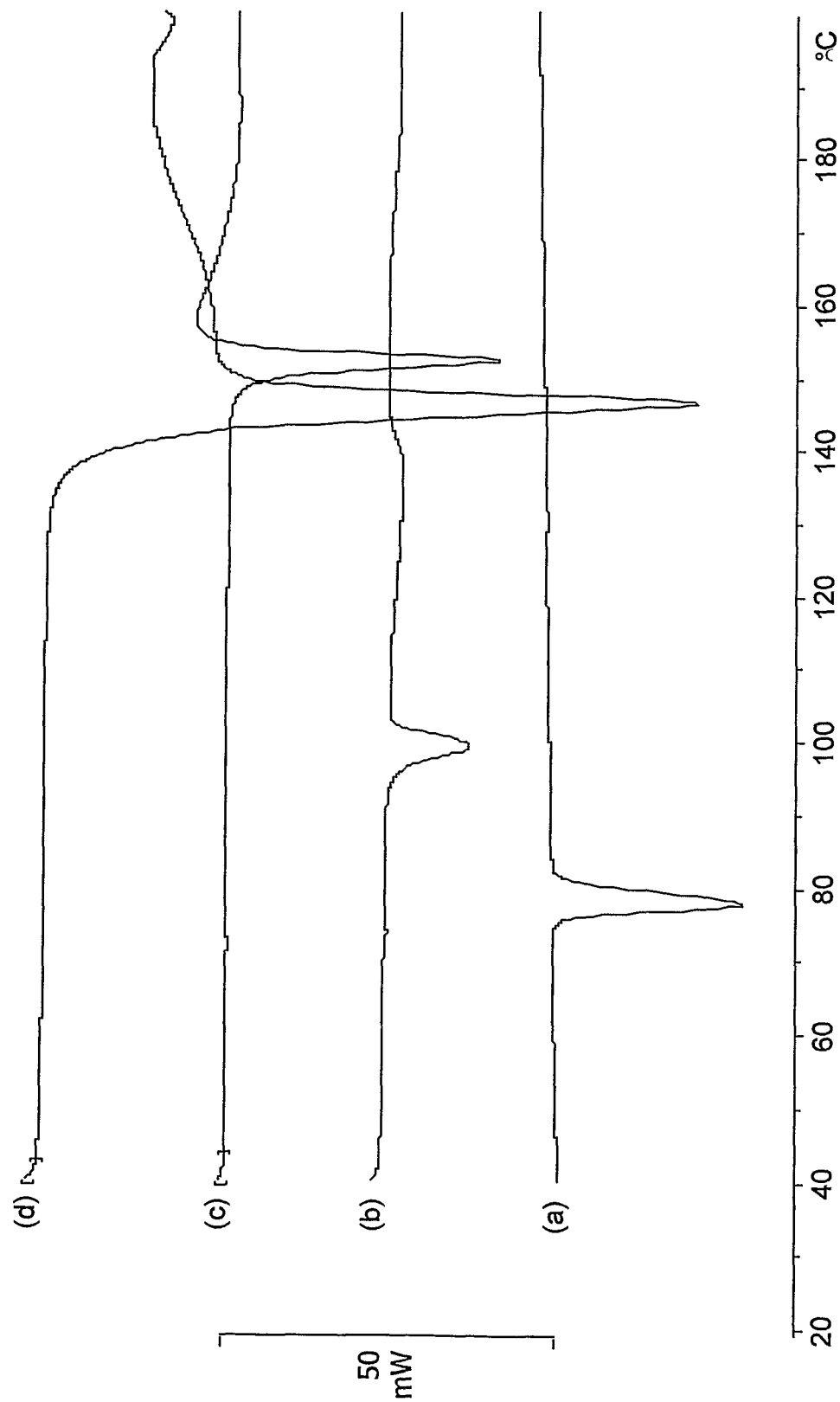
FIG. 6 shows DSC traces of Cyprodinil Form B (a), Cyprodinil-Maleic Acid Co-Crystal Form A (b) Cyprodinil-Maleic Acid Co-Crystal Form B (c) and Maleic Acid (d).

FIG. 6: DSC traces of Cyprodinil Form B (a), Cyprodinil-Maleic Acid Co-Crystal Form A (b) Cyprodinil-Maleic Acid Co-Crystal Form B (c) and Maleic Acid (d).

Table 3: 2θ values of selected peak positions of the Powder X-Ray Diffraction patterns of Cyprodinil-Maleic Acid Co-Crystal Form A and Form B.

TABLE 3

| Cyp-Maleic Acid Co-Crystal Form A 2θ | Cyp-Maleic Acid Co-Crystal Form B 2θ |
| --- | --- |
| 5.2 | 7.3 |
| 9.2 | 8.9 |
| 10.0 | 9.5 |
| 16.8 | 12.0 |
| 17.6 | 14.7 |
| 18.8 | 15.5 |
| 20.2 | 16.0 |
| 21.8 | 18.9 |
| 25.2 | 20.2 |
| 29.3 | 22.8 |

Experimental

For a 2 to 1 Co-crystal; 1 g Cyprodinil and 5 ml Acetonitrile was charged to a 30 ml vial with a magnetic stirrer and heated to 50° C. Once all the Cyprodinil had dissolved, 1.03 g Maleic Acid was added to the vial at 50° C. with stirring. The reaction mixture was cooled and allowed to stir for 48 hrs at room temperature. Any product was isolated by Buchner filtration.

For a 1 to 1 Co-crystal; 2 g Cyprodinil and 5 ml Isohexane was charged to a 30 ml vial with a magnetic stirrer and heated to 50° C. Once all the Cyprodinil had dissolved, 1.03 g Maleic Acid was added to the vial at 50° C. with stirring. The reaction mixture was cooled and allowed to stir for 48 hrs at room temperature. Any product was isolated by Buchner filtration.

3. Cyprodinil-Fumaric Acid Co-Crystal

Figure 7:
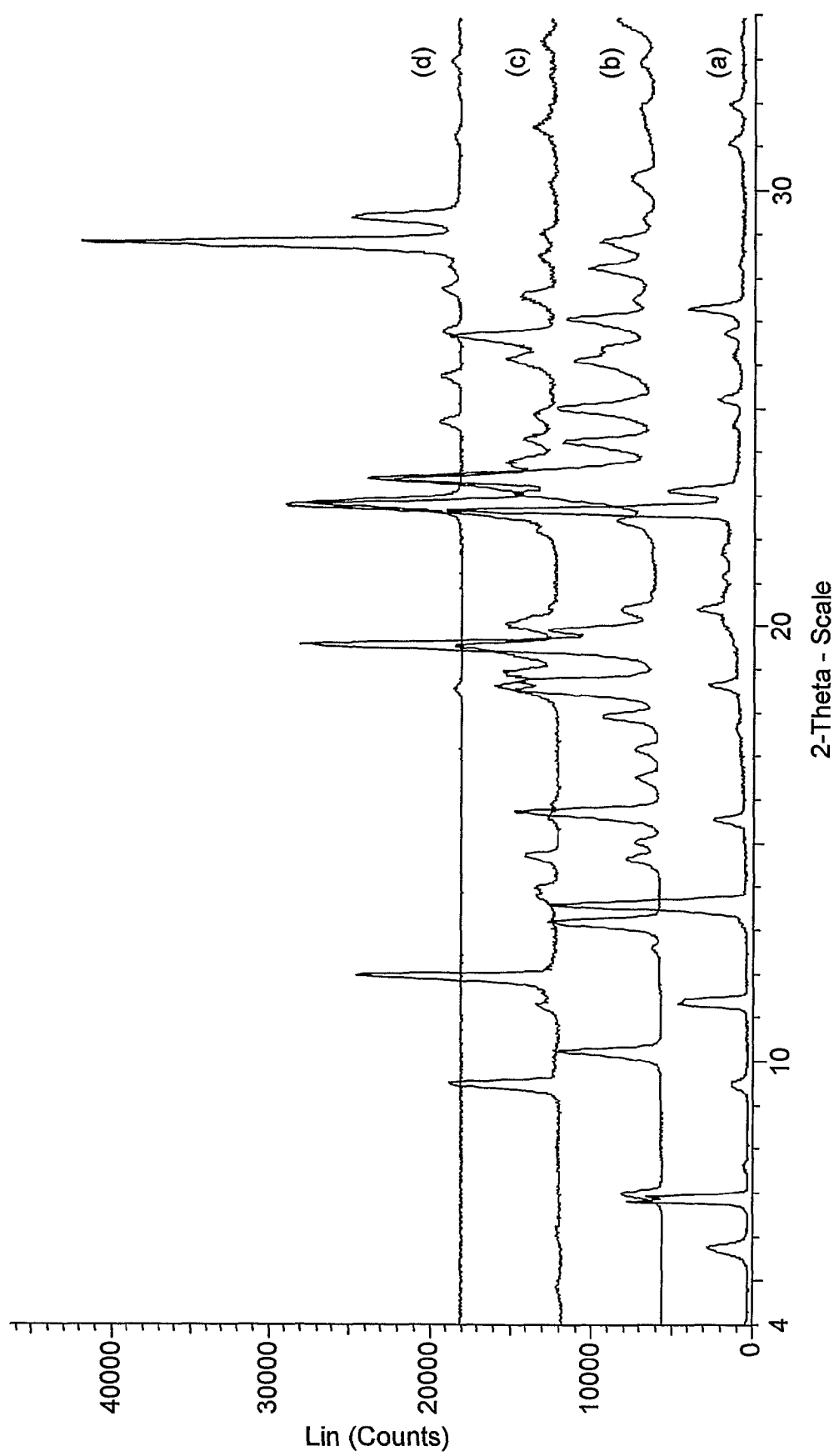
FIG. 7 shows Powder X-Ray Diffraction patterns of Cyprodinil Form A (a), Cyprodinil Form B (b), Cyprodinil-Fumaric Acid Co-Crystal Form A (c) and Fumaric acid (d).

FIG. 7: Powder X-Ray Diffraction patterns of Cyprodinil Form A (a), Cyprodinil Form B (b), Cyprodinil-Fumaric Acid Co-Crystal Form A (c) and Fumaric acid (d).

Figure 8:
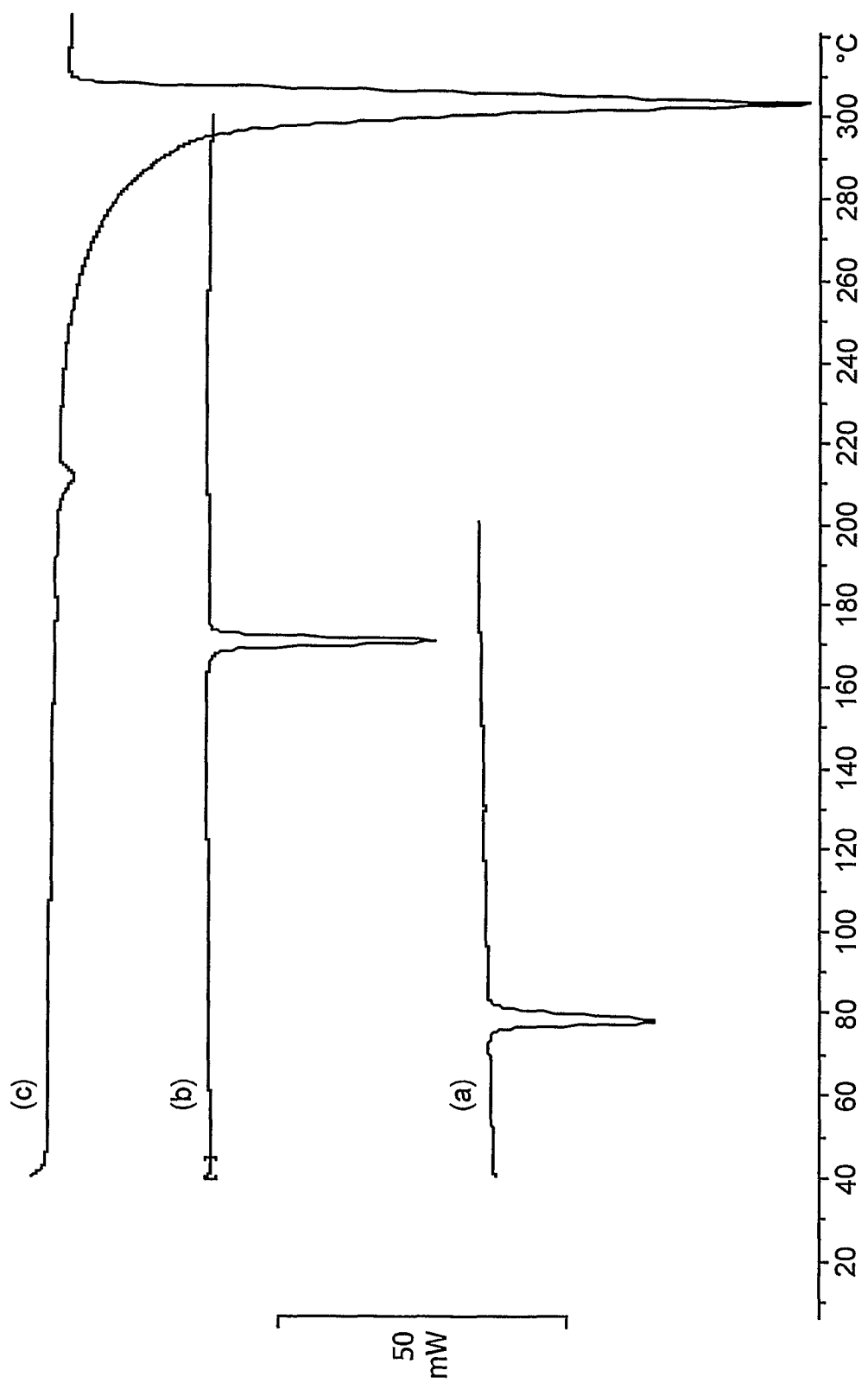
FIG. 8 shows DSC traces of Cyprodinil Form B (a), Cyprodinil-Fumaric Acid Co-Crystal Form A (b) Fumaric Acid (c).

FIG. 8: DSC traces of Cyprodinil Form B (a), Cyprodinil-Fumaric Acid Co-Crystal Form A (b) Fumaric Acid (c).

Table 4: 2θ values of selected peak positions of the Powder X-Ray Diffraction patterns of Cyprodinil-Fumaric Acid Co-Crystal Form A.

TABLE 4

| Cyprodinil-Fumaric Acid Co-Crystal Form A 2θ |
| --- |
| 9.3 |
| 12.0 |
| 14.0 |
| 14.6 |
| 18.3 |
| 18.9 |
| 19.5 |
| 20.0 |
| 22.8 |
| 23.2 |

Experimental

For a 2 to 1 Co-crystal. 1 g Cyprodinil and 5 ml Xylene was charged to a 30 ml vial with a magnetic stirrer and heated to 50° C. Once all the Cyprodinil had dissolved, 1.03 g Fumaric Acid was added to the vial at 50° C. with stirring. The reaction mixture was cooled and allowed to stir for 48 hrs at room temperature. Any product was isolated by Buchner filtration.

For a 1 to 1 Co-crystal. 2 g Cyprodinil and 5 ml Xylene was charged to a 30 ml vial with a magnetic stirrer and heated to 50° C. Once all the Cyprodinil had dissolved, 1.03 g Fumaric Acid was added to the vial at 50° C. with stirring. The reaction mixture was cooled and allowed to stir for 48 hrs at room temperature. Any product was isolated by Buchner filtration.

4 Cyprodinil-Oxalic Acid Co-Crystal

Figure 9:
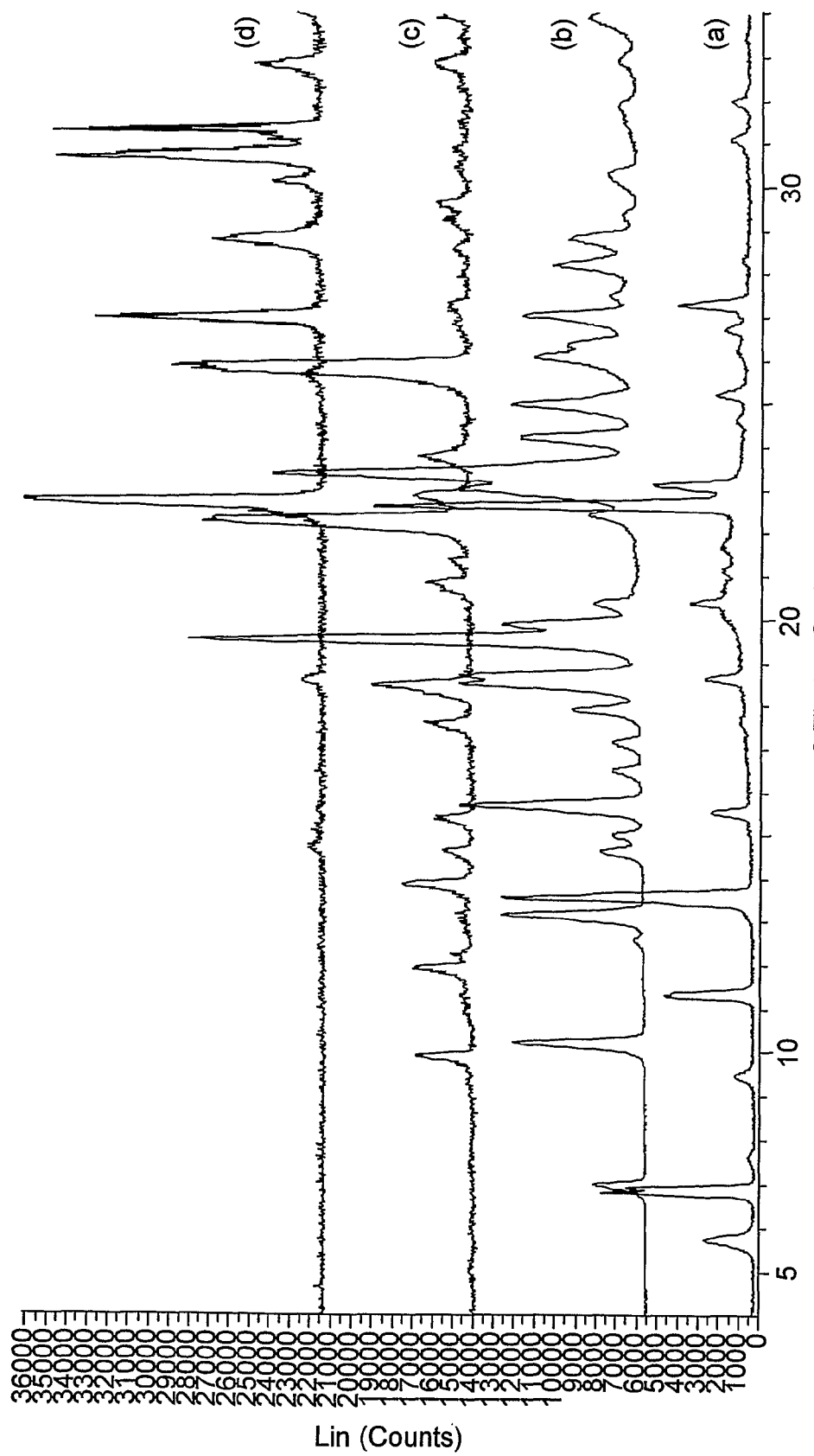
FIG. 9 shows Powder X-Ray Diffraction patterns of Cyprodinil Form A (a), Cyprodinil Form B (b), Cyprodinil-Oxalic Acid Co-Crystal Form A (c) and Oxalic acid (d).

FIG. 9: Powder X-Ray Diffraction patterns of Cyprodinil Form A (a), Cyprodinil Form B (b), Cyprodinil-Oxalic Acid Co-Crystal Form A (c) and Oxalic acid (d).

Figure 10:
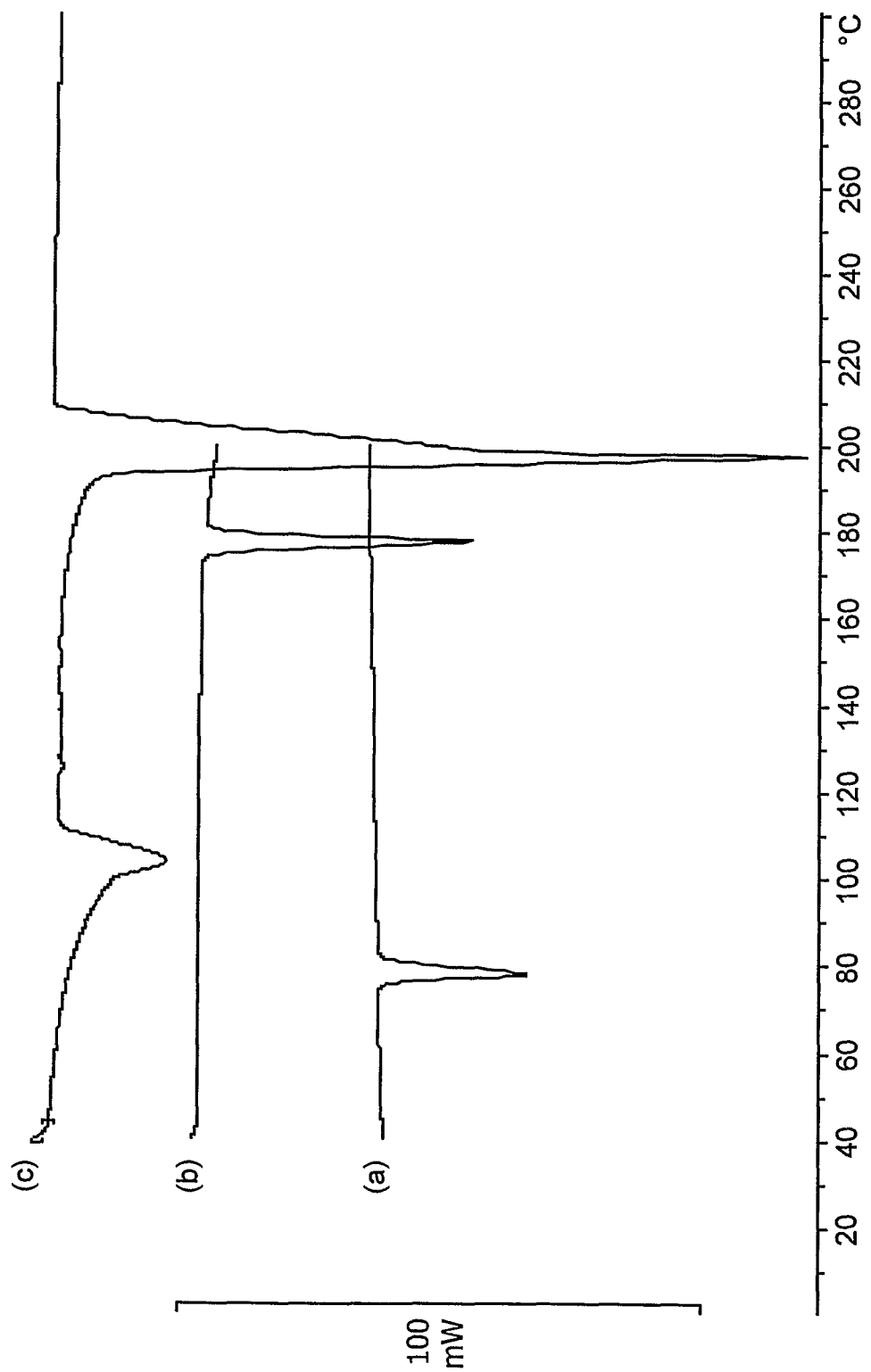
FIG. 10 shows DSC traces of Cyprodinil Form B (a), Cyprodinil-oxalic Acid Co-Crystal Form A (b) oxalic Acid (c).

FIG. 10: DSC traces of Cyprodinil Form B (a), Cyprodinil-oxalic Acid Co-Crystal Form A (b) oxalic Acid (c).

Table 5: 2θ values of selected peak positions of the Powder X-Ray Diffraction patterns of Cyprodinil-Oxalic Acid Co-Crystal Form A.

TABLE 5

| Cyp-Oxalic Acid Co-Crystal Form A 2θ |
| --- |
| 10.0 |
| 12.0 |
| 13.9 |
| 14.6 |
| 15.3 |
| 17.7 |
| 18.3 |
| 22.2 |
| 22.7 |
| 23.8 |

Experimental

For a 2 to 1 Co-crystal. 2 g Cyprodinil and 5 ml THF was charged to a 30 ml vial with a magnetic stirrer and heated to 50° C. Once all the Cyprodinil had dissolved, 0.4 g Oxalic Acid was added to the vial at 50° C. with stirring. The reaction mixture was cooled and allowed to stir for 48 hrs at room temperature. Any product was isolated by Buchner filtration.

For a 1 to 1 Co-crystal. 2 g Cyprodinil and 5 ml THF was charged to a 30 ml vial with a magnetic stirrer and heated to 50° C. Once all the Cyprodinil had dissolved, 0.8 g Oxalic Acid was added to the vial at 50° C. with stirring. The reaction mixture was cooled and allowed to stir for 48 hrs at room temperature. Any product was isolated by Buchner filtration.

5. Cyprodinil-Pyrazine Carboxylic Acid Co-Crystal

Figure 11:
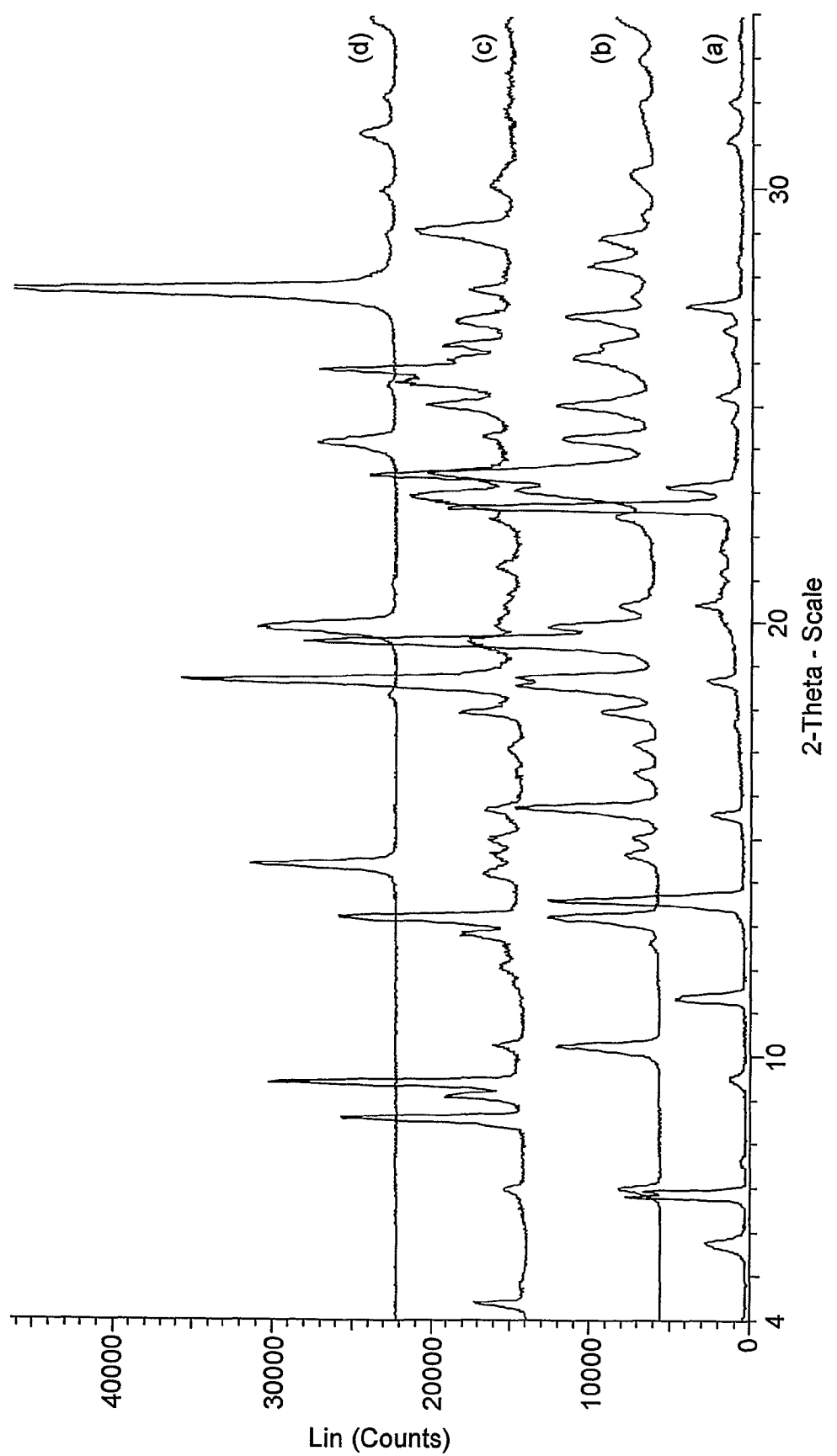
FIG. 11 shows Powder X-Ray Diffraction patterns of Cyprodinil Form A (a), Cyprodinil Form B (b), Cyprodinil-Pyrazine carboxylic Acid Co-Crystal Form A (c) and Pyrazine carboxylic acid (d).

FIG. 11: Powder X-Ray Diffraction patterns of Cyprodinil Form A (a), Cyprodinil Form B (b), Cyprodinil-Pyrazine carboxylic Acid Co-Crystal Form A (c) and Pyrazine carboxylic acid (d).

Figure 12:
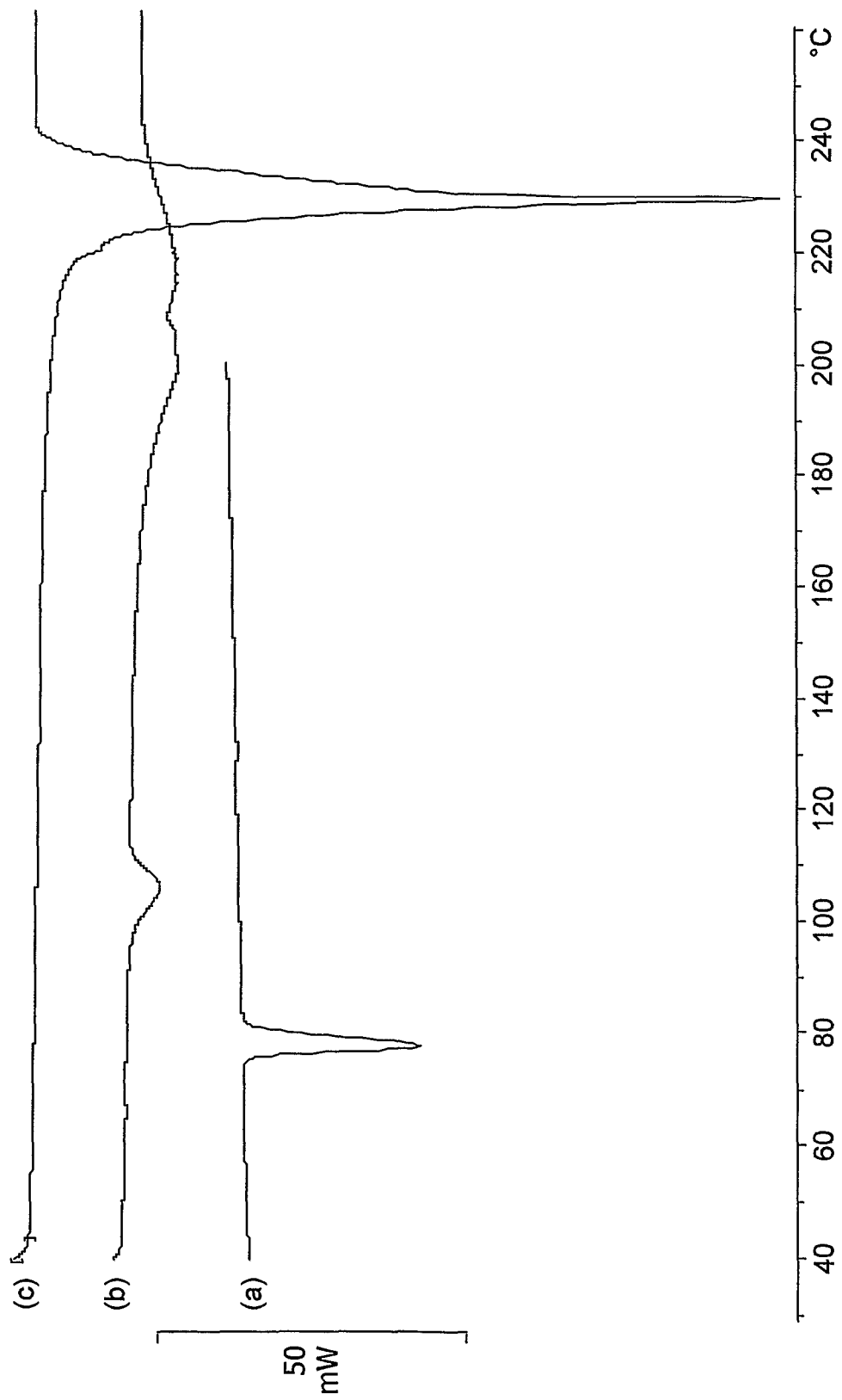
FIG. 12 shows DSC traces of Cyprodinil Form B (a), Cyprodinil-Pyrazine carboxylic Acid Co-Crystal Form A (b) Pyrazine carboxylic Acid (c).

FIG. 12: DSC traces of Cyprodinil Form B (a), Cyprodinil-Pyrazine carboxylic Acid Co-Crystal Form A (b) Pyrazine carboxylic Acid (c).

Table 6: 2θ values of selected peak positions of the Powder X-Ray Diffraction patterns of Cyprodinil-Pyrazine carboxylic Acid Co-Crystal Form A

TABLE 6

| Cyprodinil-Pyrazine carboxylic Acid Co-Crystal Form A 2θ |
| --- |
| 4.3 |
| 8.5 |
| 9.0 |
| 9.3 |
| 12.7 |
| 13.1 |
| 18.0 |
| 18.7 |
| 19.5 |
| 25.9 |

Experimental

For a 1 to 1 Co-crystal. 2 g Cyprodinil and 5 ml Ethanol was charged to a 30 ml vial with a magnetic stirrer and heated to 50° C. Once all the Cyprodinil had dissolved, 1.10 g Pyrazine Carboxylic Acid was added to the vial at 50° C. with stirring. The reaction mixture was cooled and allowed to stir for 48 hrs at room temperature. Any product was isolated by Buchner filtration.

For a 2 to 1 Co-crystal. 1 g Cyprodinil and 5 ml Acetonitrile was charged to a 30 ml vial with a magnetic stirrer and heated to 50° C. Once all the Cyprodinil had dissolved, 0.55 g Pyrazine Carboxylic Acid was added to the vial at 50° C. with stirring. The reaction mixture was cooled and allowed to stir for 48 hrs at room temperature. Any product was isolated by Buchner filtration.

6. Cyprodinil-Succinic Acid Co-Crystal

Figure 13:
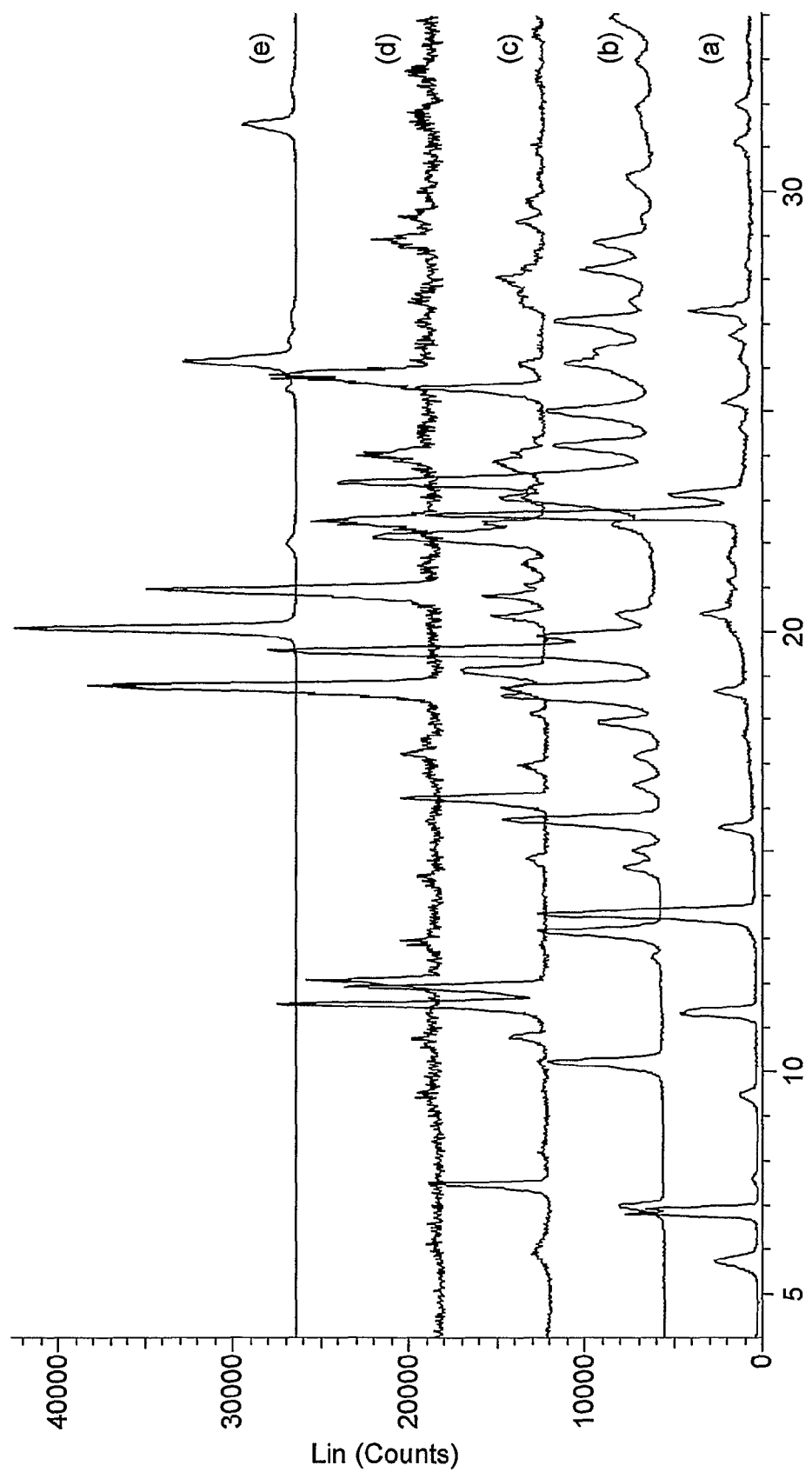
FIG. 13 shows Powder X-Ray Diffraction patterns of Cyprodinil Form A (a), Cyprodinil Form B (b), Cyprodinil-Succinic Acid Co-Crystal Form A (c) and Cyprodinil-Succinic Acid Co-Crystal Form B (d) and Succinic acid (e).

FIG. 13: Powder X-Ray Diffraction patterns of Cyprodinil Form A (a), Cyprodinil Form B (b), Cyprodinil-Succinic Acid Co-Crystal Form A (c) and Cyprodinil-Succinic Acid Co-Crystal Form B (d) and Succinic acid (e).

Table 7: 2θ values of selected peak positions of the Powder X-Ray Diffraction patterns of Cyprodinil-Succinic Acid Co-Crystal Form A and Form B.

TABLE 7

| Cyprodinil-Succinic Acid Co-Crystal Form A 2θ | Cyprodinil-Succinic Acid Co-Crystal Form B 2θ |
| --- | --- |
| 7.3 | 12.5 |
| 10.8 | 17.3 |
| 11.5 | 18.7 |
| 11.9 | 21.0 |
| 16.1 | 22.4 |
| 16.9 | 24.0 |
| 19.1 | 25.4 |
| 20.2 | 28.8 |
| 20.7 | 29.3 |
| 22.0 | |

Experimental

For a 1 to 1 Co-crystal. 2 g Cyprodinil and 5 ml Methanol was charged to a 30 ml vial with a magnetic stirrer and heated to 50° C. Once all the Cyprodinil had dissolved, 2.0 g Succinic Acid was added to the vial at 50° C. with stirring. The reaction mixture was cooled and allowed to stir for 48 hrs at room temperature. Any product was isolated by Buchner filtration.

7. Cyprodinil-Levulinic Acid Co-Crystal

Figure 14:
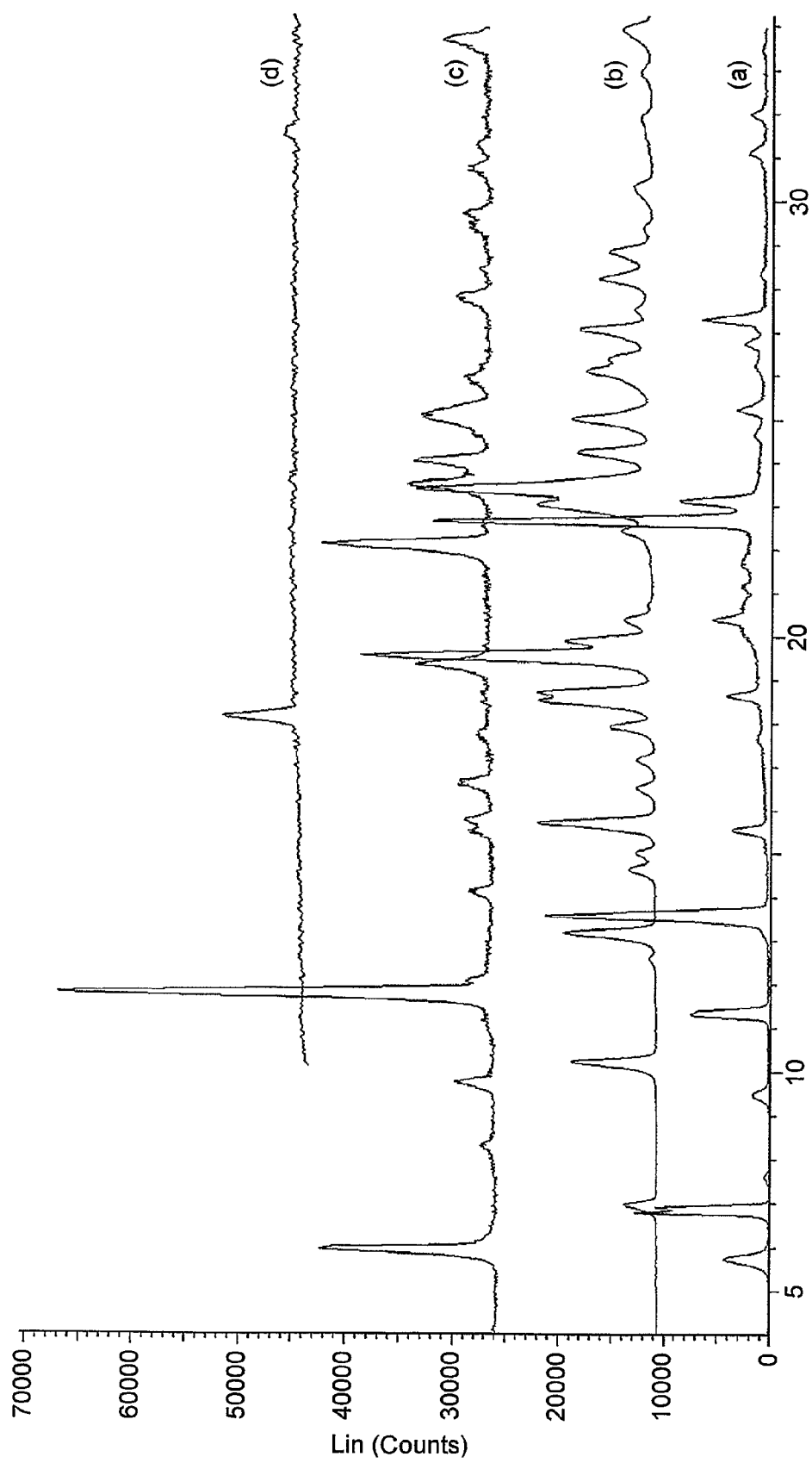
FIG. 14 shows Powder X-Ray Diffraction patterns of Cyprodinil Form A (a), Cyprodinil Form B (b), Cyprodinil-Levulinic acid Co-Crystal Form B (c) and Levulinic acid (d).

FIG. 14: Powder X-Ray Diffraction patterns of Cyprodinil Form A (a), Cyprodinil Form B (b), Cyprodinil-Levulinic acid Co-Crystal Form B (c) and Levulinic acid (d).

Table 8: 2θ values of selected peak positions of the Powder X-Ray Diffraction patterns of Cyprodinil-Levulinic acid Co-Crystal.

TABLE 8

| Cyprodinil-Levulinic Acid Co-crystal (2θ) |
| --- |
| 5.9 |
| 9.8 |
| 11.8 |
| 14.2 |
| 15.8 |
| 16.7 |
| 19.3 |
| 22.2 |
| 23.6 |
| 24.0 |
| 25.1 |
| 26.0 |
| 27.8 |
| 29.7 |
| 30.8 |
| 33.7 |

Figure 15:
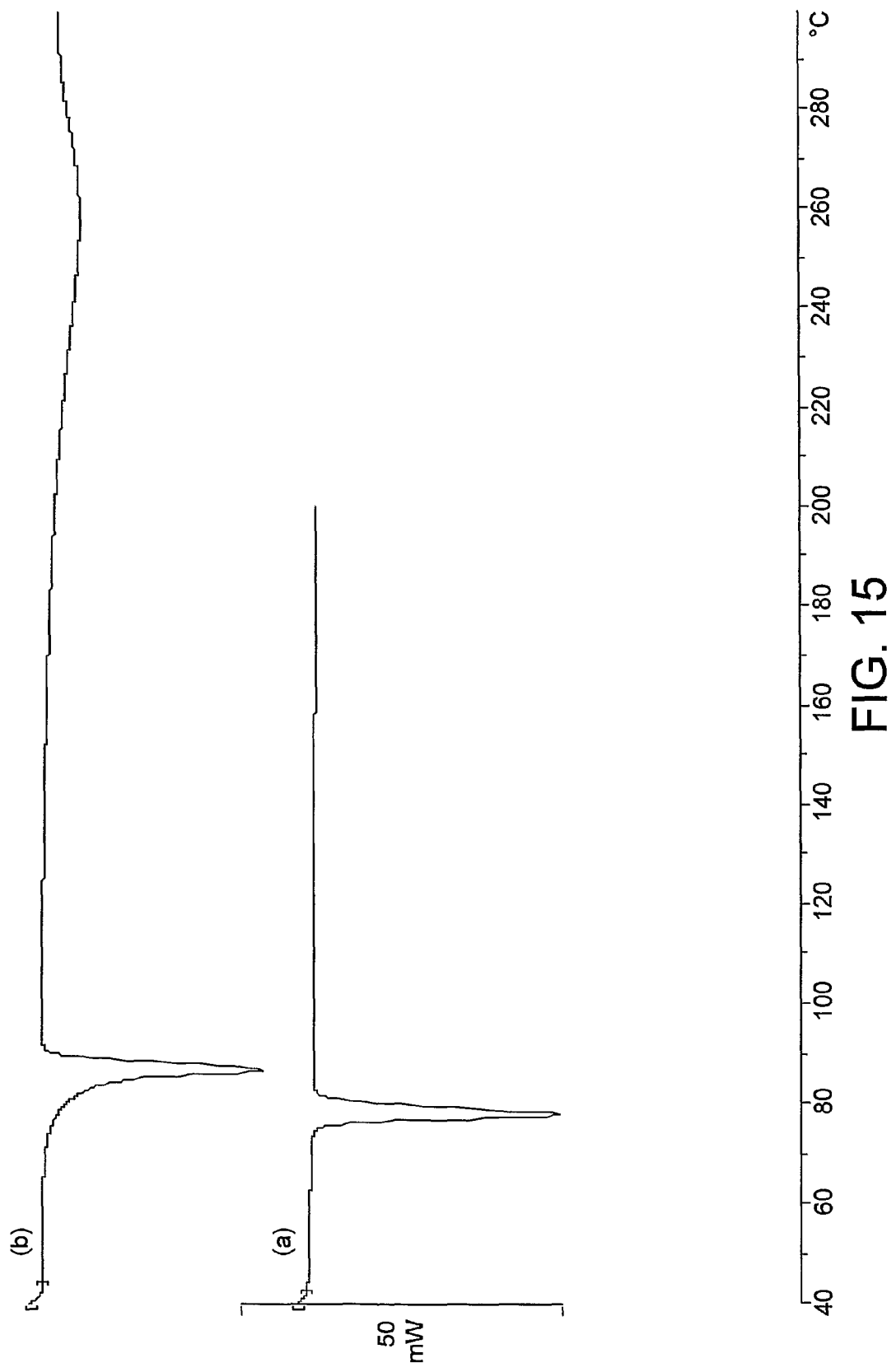
FIG. 15 shows DSC traces of Cyprodinil Form B (a) and Cyprodinil-Levulinic Acid Co-Crystal Form B (b).

FIG. 15: DSC traces of Cyprodinil Form B (a) and Cyprodinil-Levulinic Acid Co-Crystal Form B (b).

Experimental

For a 2:1 Co-Crystal by Evaporative Crystallisation 2.0 g of CYP was added to a 40 ml vial with 5 ml Acetone.

1.9 g of Levulinic acid in 5 ml ethyl acetate was added to this mixture.

The sample was kept at 50° C. for 2 hours and then allowed to cool, and evaporate, before being filtered on a Buchner.

8 Cyprodinil-4-hydroxy-4-biphenylcarboxylic acid co-crystal

Figure 16:
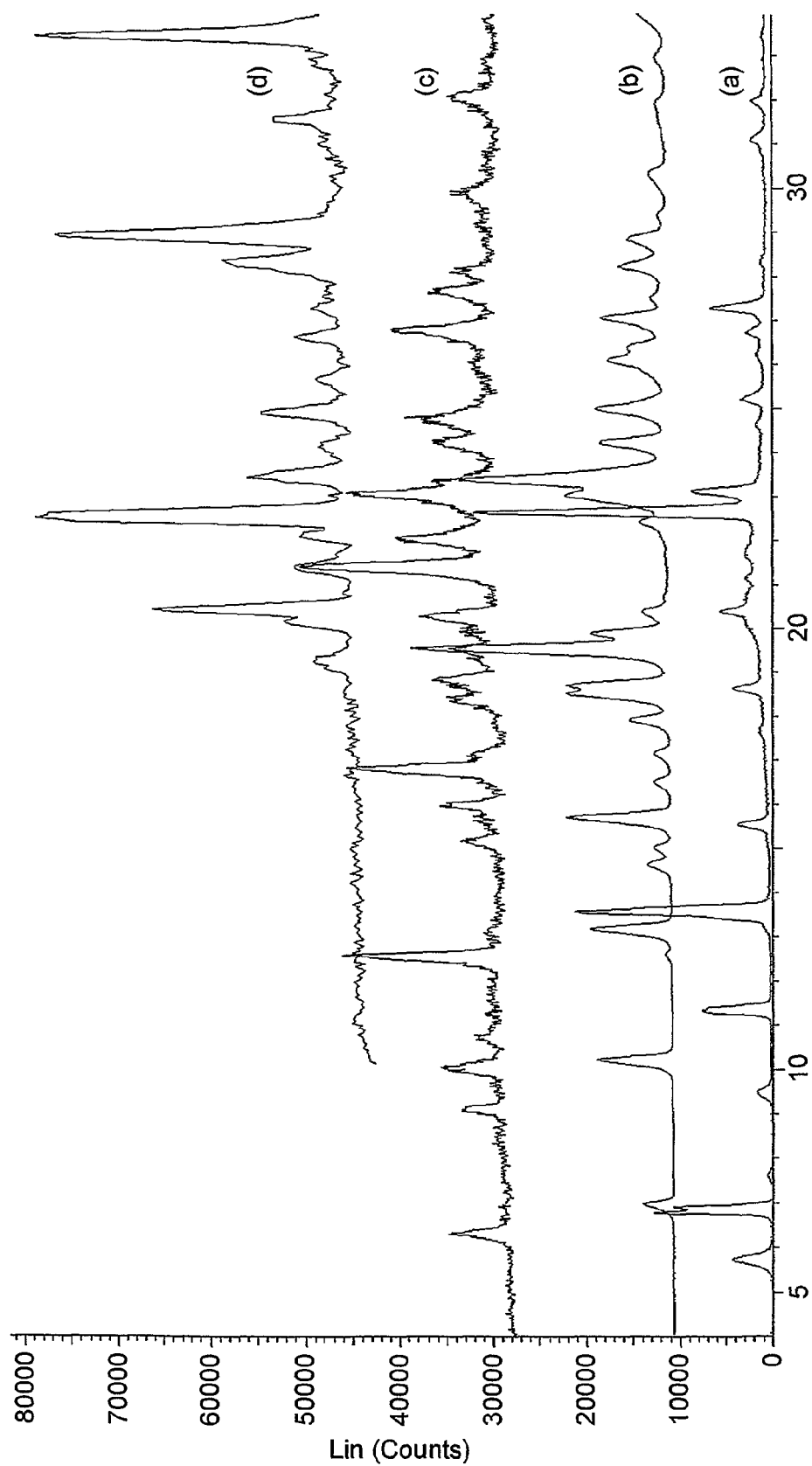
FIG. 16 shows Powder X-Ray Diffraction patterns of Cyprodinil Form A (a), Cyprodinil Form B (b), Cyprodinil-4-hydroxy-4-biphenylcarboxylic acid Co-Crystal Form B (c) and 4-hydroxy-4-biphenylcarboxylic acid (d).

FIG. 16: Powder X-Ray Diffraction patterns of Cyprodinil Form A (a), Cyprodinil Form B (b), Cyprodinil-4-hydroxy-4-biphenylcarboxylic acid Co-Crystal Form B (c) and 4-hydroxy-4-biphenylcarboxylic acid (d).

Table 9: 2θ values of selected peak positions of the Powder X-Ray Diffraction patterns of Cyprodinil-4-hydroxy-4-biphenylcarboxylic acid Co-Crystal.

TABLE 9

| Cyprodinil-4-hydroxy-4-biphenylcarboxylic acid Co-crystal 2θ |
| --- |
| 6.3 |
| 9.2 |
| 10.0 |
| 12.6 |
| 15.2 |
| 16.0 |
| 16.9 |
| 18.8 |
| 20.3 |
| 21.4 |

TABLE 9-continued

| Cyprodinil-4-hydroxy-4-biphenylcarboxylic acid Co-crystal 2θ |
| --- |
| 22.1 |
| 23.1 |
| 24.3 |
| 24.9 |
| 26.8 |
| 27.7 |
| 28.1 |

Figure 17:
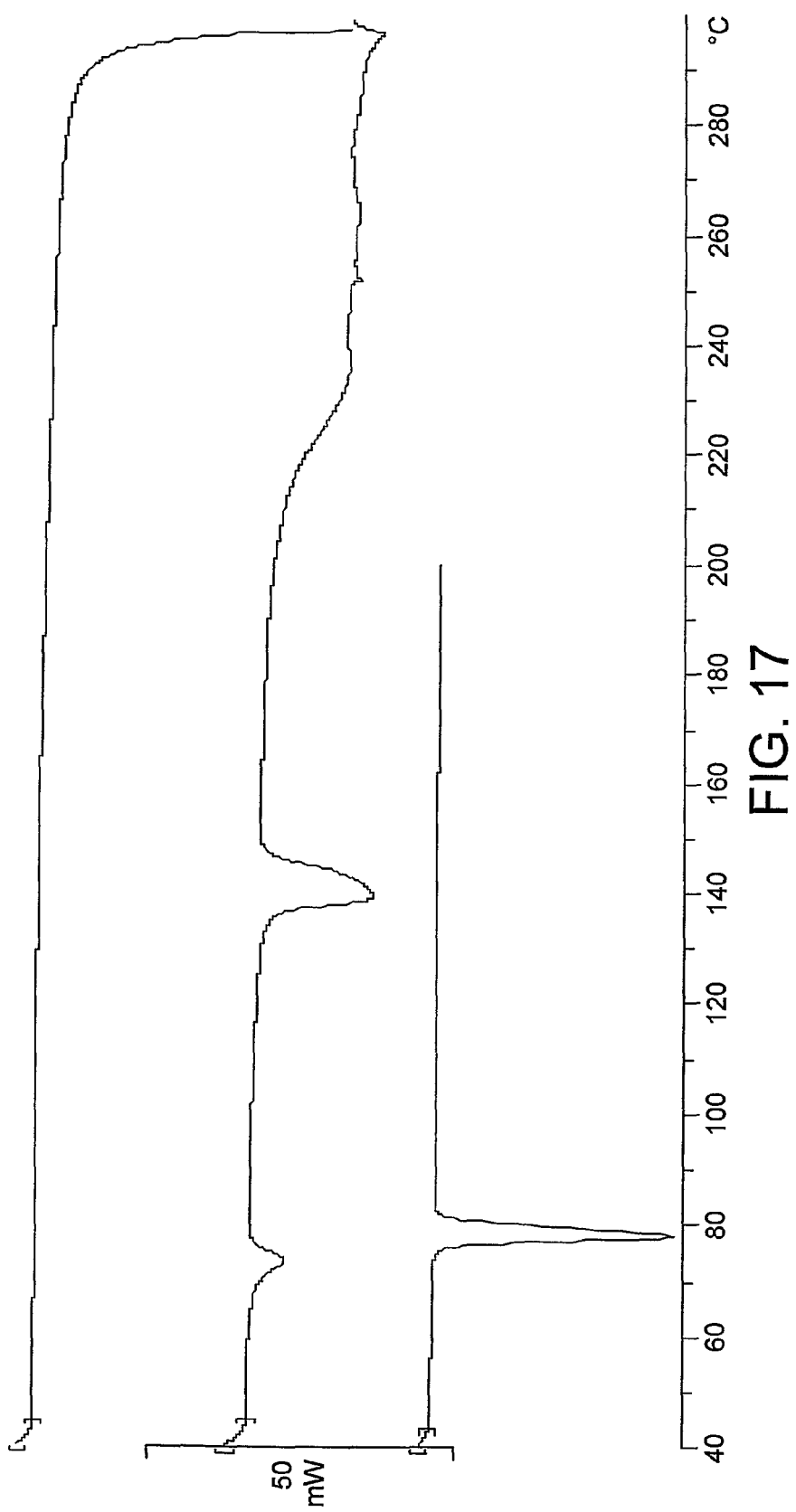
FIG. 17 shows DSC traces of Cyprodinil Form B (a), Cyprodini-1-4-hydroxy-4-biphenylcarboxylic acid Co-Crystal Form B (b) and 4-hydroxy-4-biphenylcarboxylic acid (c).

FIG. 17: DSC traces of Cyprodinil Form B (a), Cyprodinil-4-hydroxy-4-biphenylcarboxylic acid Co-Crystal Form B (b) and 4-hydroxy-4-biphenylcarboxylic acid (c).

Experimental

For a 1:1 Co-Crystal by Cooling Crystallisation 1.0 of CYP was added to a 40 ml vial with 5 ml Acetone.

1.1 g of 4-hydroxy-4-biphenylcarboxylic acid in 5 ml methanol was added to this mixture.

The sample was kept at 50° C. for 2 hours, then kept at 40° C. for an hour, then kept at 30° C. for an hour, and then finally kept at 20° C. for an hour, before being left overnight in the fridge. The product was then isolated on a Buchner.

9. Cyprodinil-(2-methylphenoxy)acetic acid co-crystal

Figure 18:
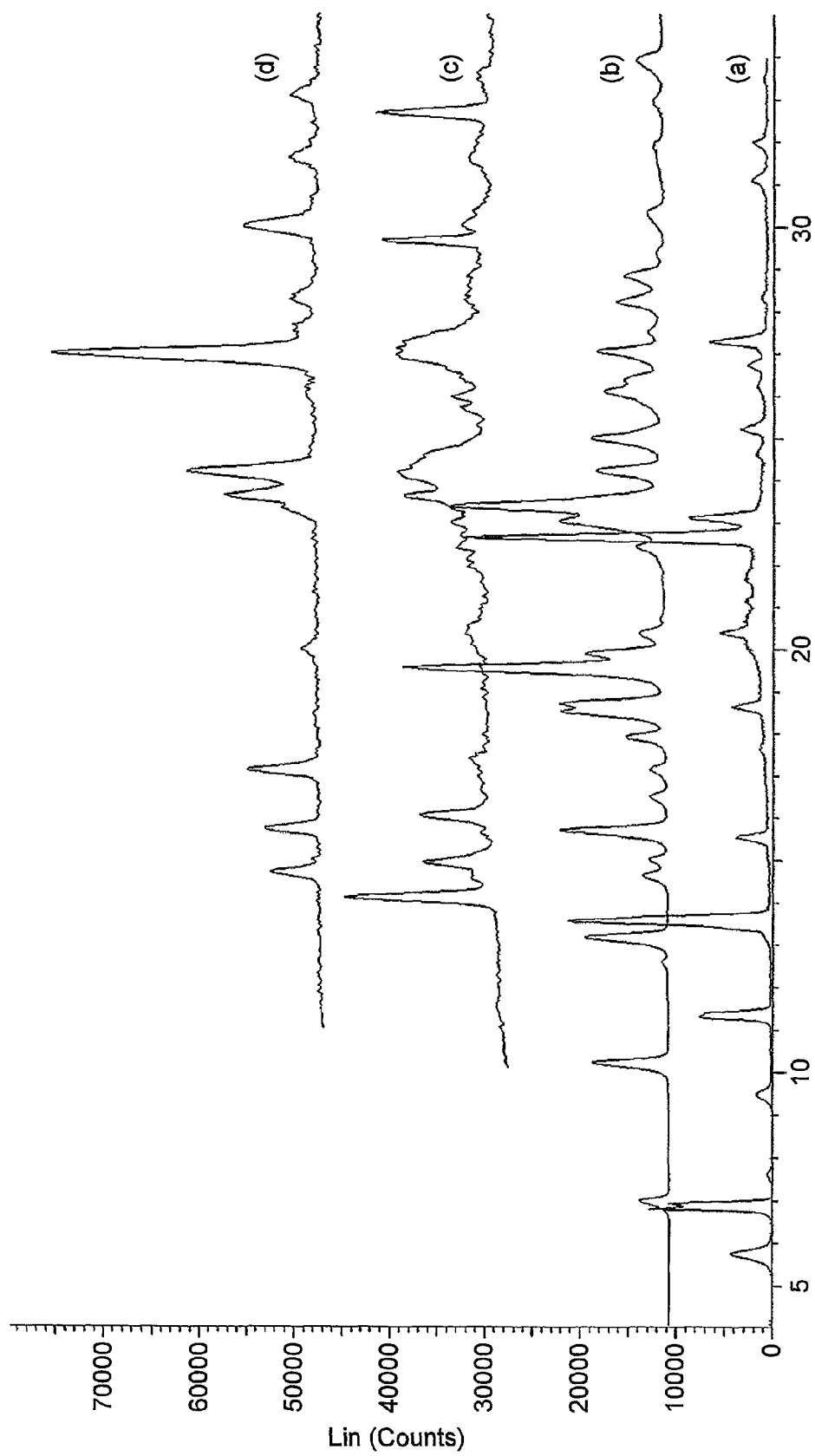
FIG. 18 shows Powder X-Ray Diffraction patterns of Cyprodinil Form A (a), Cyprodinil Form B (b), Cyprodinil-(2-methoxyphenoxy)acetic acid Co-Crystal Form B (c) and (2-methoxyphenoxy) acetic acid (d).

FIG. 18: Powder X-Ray Diffraction patterns of Cyprodinil Form A (a), Cyprodinil Form B (b), Cyprodinil-(2-methoxyphenoxy)acetic acid Co-Crystal Form B (c) and (2-methoxyphenoxy)acetic acid (d).

Table 10: 2θ values of selected peak positions of the Powder X-Ray Diffraction patterns of Cyprodinil-(2-methoxyphenoxy)acetic acid Co-Crystal.

TABLE 10

| Cyprodinil-(2-methoxyphenoxy)acetic acid co-crystal 2θ |
| --- |
| 14.1 |
| 15.0 |
| 16.0 |
| 23.6 |
| 24.1 |
| 27.0 |
| 29.7 |
| 32.7 |

Experimental

For a 1:2 Co-Crystal by Cooling Crystallisation

100 μl of a 27.5% CYP in acetone solution was added to a well in a 96 well plate.

101 μl of a 10% (2-methoxyphenoxy)acetic acid in methanol solution was added to this mixture with a further 75 μl of xylene. The sample was kept at 50° C. for 2 hours, then cooled to 10° C. overnight and the remaining liquid was removed.

10. Cyprodinil-Hexadecanoic Acid Co-Crystal

Figure 19:
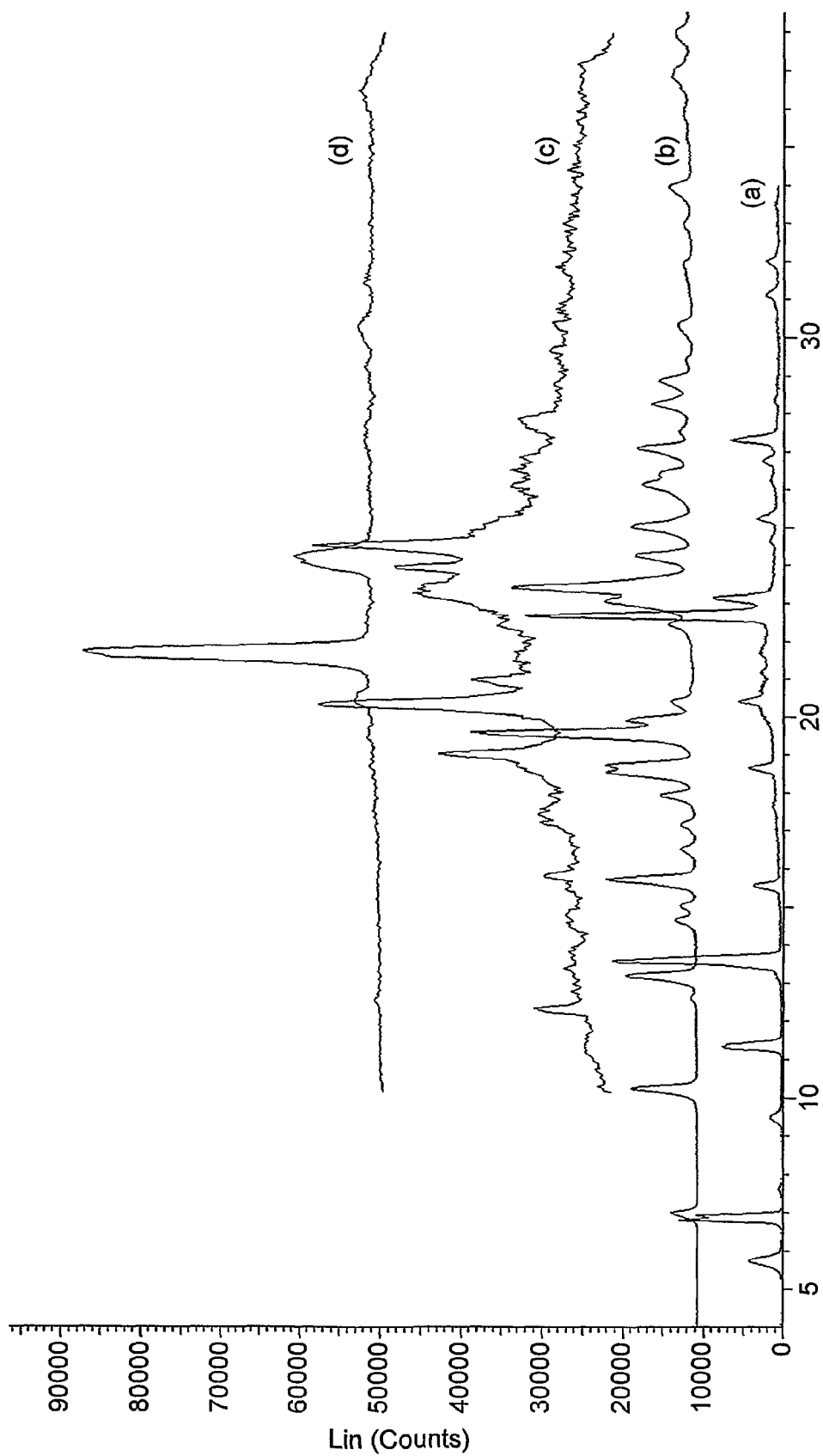
FIG. 19 shows Powder X-Ray Diffraction patterns of Cyprodinil Form A (a), Cyprodinil Form B (b), Cyprodinil-hexadecanoic acid Co-Crystal Form B (c) and hexadecanoic acid (d).

FIG. 19: Powder X-Ray Diffraction patterns of Cyprodinil Form A (a), Cyprodinil Form B (b), Cyprodinil-hexadecanoic acid Co-Crystal Form B (c) and hexadecanoic acid (d).

Table 11: 2θ values of selected peak positions of the Powder X-Ray Diffraction patterns of Cyprodinil-hexadecanoic acid Co-Crystal.

TABLE 11

| Cyprodinil-Hexadecanoic acid co-crystal 2θ |
| --- |
| 12.2 |
| 18.9 |
| 20.2 |
| 21.0 |
| 23.3 |
| 24.0 |
| 24.5 |
| 27.9 |

Experimental

For a 2:1 Co-Crystal by Cooling Crystallisation

100 μl of a 27.5% Cyprodinil in acetone solution was added to a well in a 96 well plate.

311 μl of a 5% Hexadecanoic acid in methanol solution was added to this mixture with a further 75 μl of methanol. The sample was kept at 50° C. for 2 hours, then cooled to 10° C. overnight and the remaining liquid was removed.

11. Cyprodinil 4-(Methylamino)benzoic acid co-crystal

Figure 20:
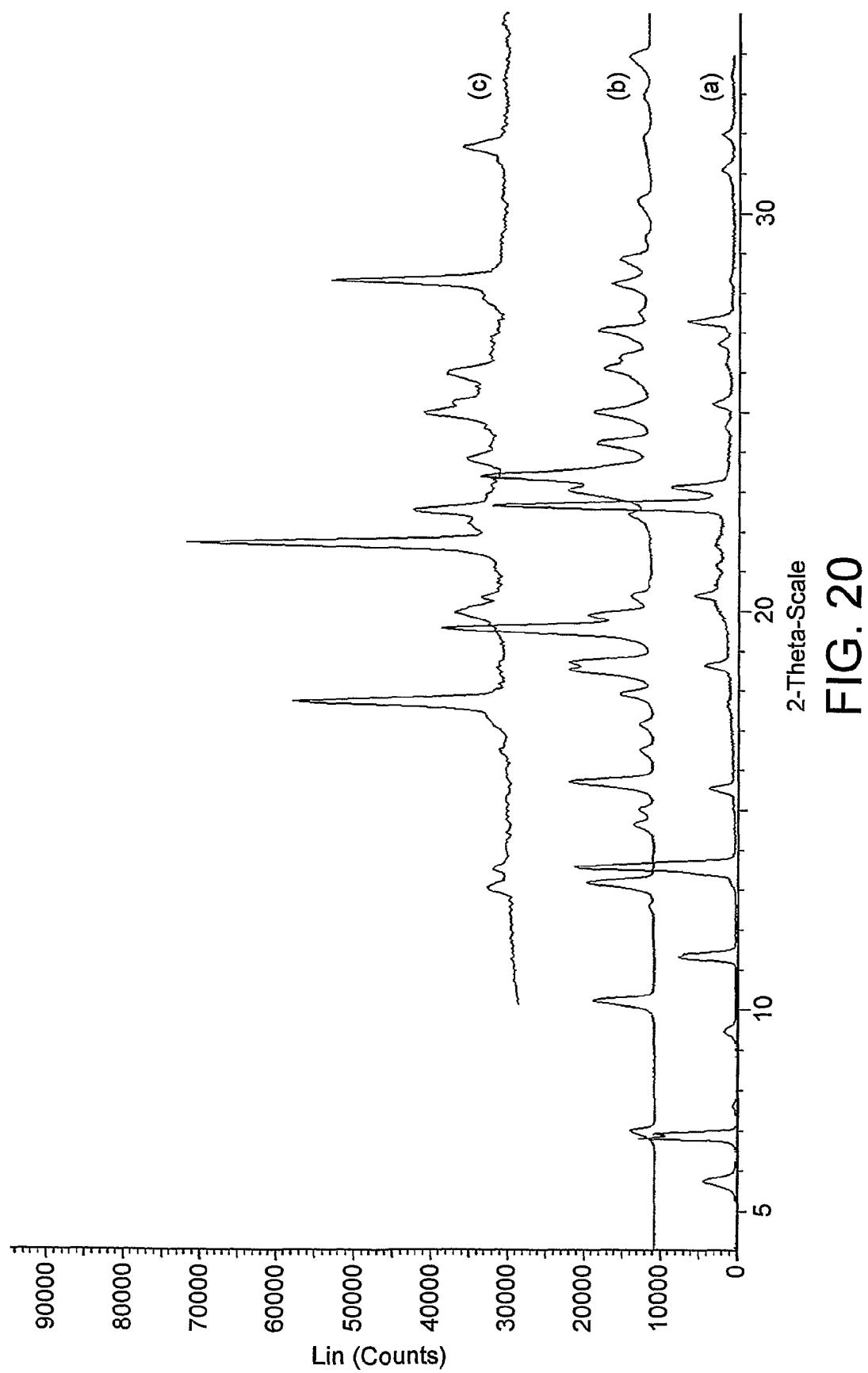
FIG. 20 shows Powder X-Ray Diffraction patterns of Cyprodinil Form A (a), Cyprodinil Form B (b) and Cyprodinil-4-(Methylamino)benzoic acid Co-Crystal Form B (c).

FIG. 20: Powder X-Ray Diffraction patterns of Cyprodinil Form A (a), Cyprodinil Form B (b) and Cyprodinil-4-(Methylamino)benzoic acid Co-Crystal Form B (c)

Table 12: 2θ values of selected peak positions of the Powder X-Ray Diffraction patterns of Cyprodinil-4(methylamonio) benzoic acid Co-Crystal.

TABLE 12

| Cyprodinil-4(methylamonio) benzoic acid co-crystal 2θ |
| --- |
| 13.0 |
| 17.7 |
| 20.0 |
| 21.7 |
| 22.6 |
| 23.8 |
| 25.0 |
| 26.1 |
| 28.3 |
| 31.7 |

Experimental

For a 1:1 Co-Crystal by Cooling Crystallisation

100 μl of a 27.5% Cyprodinil in acetone solution was added to a well in 96 well plate.

366 μl of a 5% 4(methylamonio) benzoic acid in methanol solution was added to this mixture with a further 75 μl of xylene. The sample was kept at 50° C. for 2 hours, then cooled to 10° C. overnight.

12 Cyprodinil-Trimethylacetic Acid Co-Crystal

Figure 21:
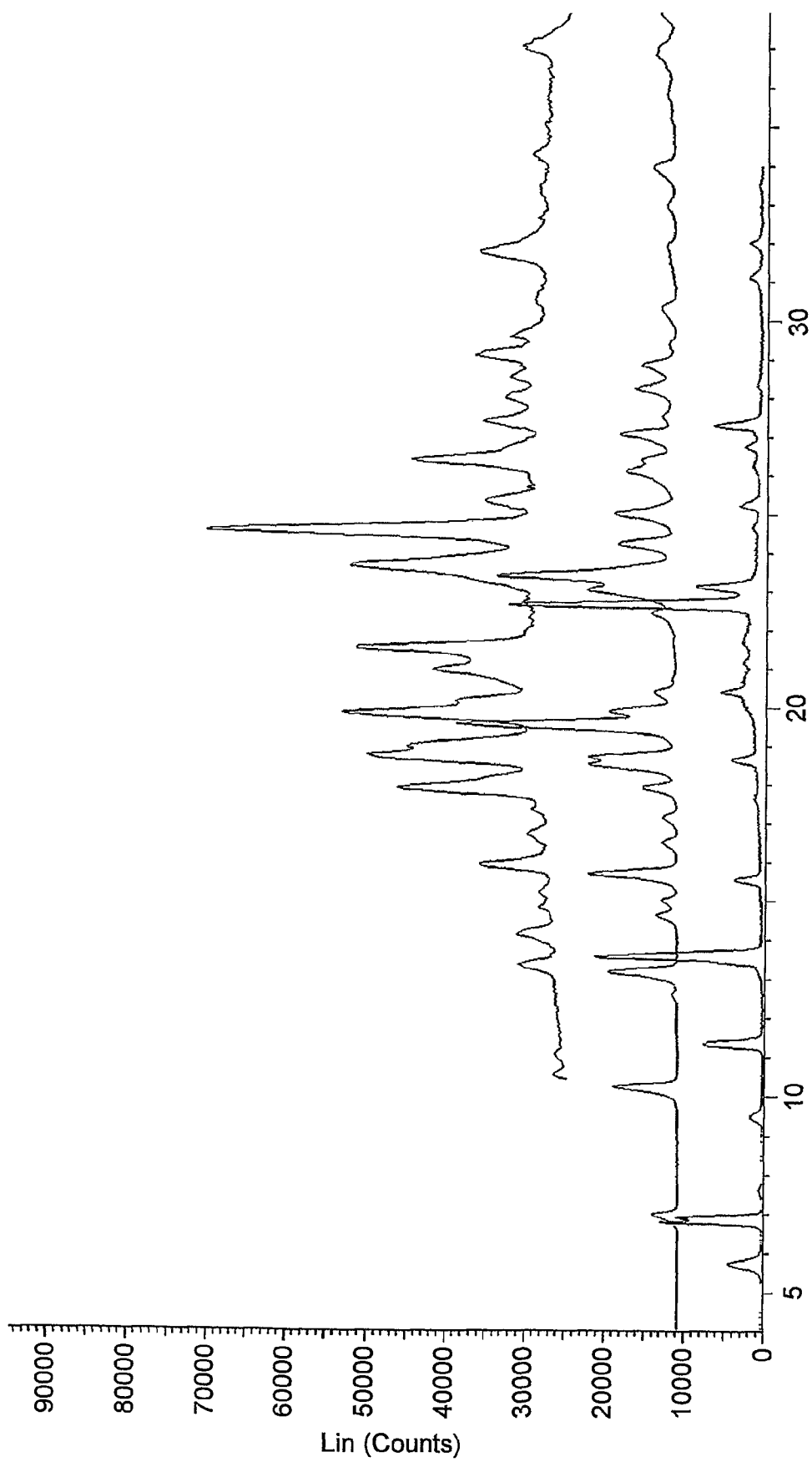
FIG. 21 shows Powder X-Ray Diffraction patterns of Cyprodinil Form A (a), Cyprodinil Form B (b) and Cyprodinil-Trimethylacetic acid Co-Crystal Form B (c).

FIG. 21: Powder X-Ray Diffraction patterns of Cyprodinil Form A (a), Cyprodinil Form B (b) and Cyprodinil-Trimethylacetic acid Co-Crystal Form B (c)

Table 13: 2θ values of selected peak positions of the Powder X-Ray Diffraction patterns of Cyprodinil-Trimethylacetic acid Co-Crystal.

TABLE 13

| Cyprodinil-Trimethylacetic acid co-crystal |
|---|
| 2θ |
| 13.2 |
| 14.2 |
| 15.9 |
| 16.8 |
| 18.0 |
| 18.8 |
| 19.9 |
| 20.9 |
| 21.5 |
| 23.7 |
| 24.6 |
| 25.4 |
| 26.5 |
| 27.4 |
| 28.1 |
| 29.1 |
| 31.8 |
| 37.0 |

Experimental

For a 1:1 Co-Crystal by Evaporative Crystallisation

100 µl of a 27.5% Cyprodinil in acetone solution was added to a well in 96 well plate.

124 µl of a 10% Trimethylacetic acid in methanol solution was added to this mixture with a further 500 µl of acetonitrile. The sample was kept at 50° C. for 2 hours and then allowed to cool and evaporate.

13. Cyprodinil-Pyruvic Acid Co-Crystal

Figure 22:
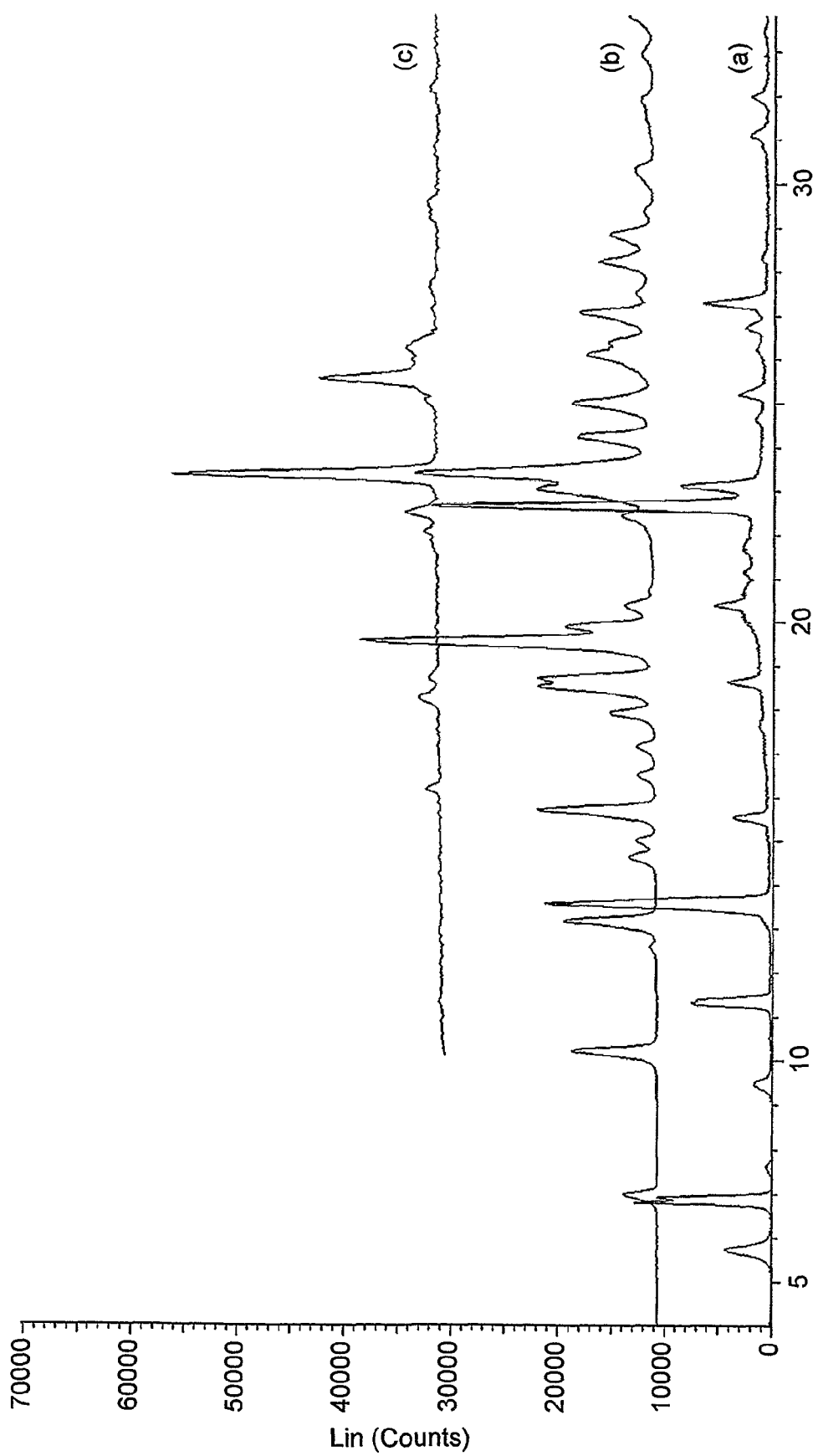
FIG. 22 shows Powder X-Ray Diffraction patterns of Cyprodinil Form A (a), Cyprodinil Form B (b) and Cyprodinil-Pyruvic acid Co-Crystal Form B (c).

FIG. 22: Powder X-Ray Diffraction patterns of Cyprodinil Form A (a), Cyprodinil Form B (b) and Cyprodinil-Pyruvic acid Co-Crystal Form B (c)

Table 14: 2θ values of selected peak positions of the Powder X-Ray Diffraction patterns of Cyprodinil-Pyruvic acid Co-Crystal.

TABLE 14

| Cyp-Pyruvic acid co-crystal |
|---|
| 2θ |
| 16.2 |
| 18.3 |
| 22.5 |
| 23.4 |
| 25.6 |
| 26.3 |

Experimental

For a 1:2 Co-Crystal by Evaporative Crystallisation

100 µl of a 27.5% CYP in acetone solution was added to a well in 96 well plate.

195 µl of a 10% Trimethylacetic acid in ethanol solution was added to this mixture with a further 500 µl of xylene. The sample was kept at 50° C. for 2 hours and then allowed to cool and evaporate.

14 Cyprodinil-Glycolic Acid Co-Crystal

Figure 23:
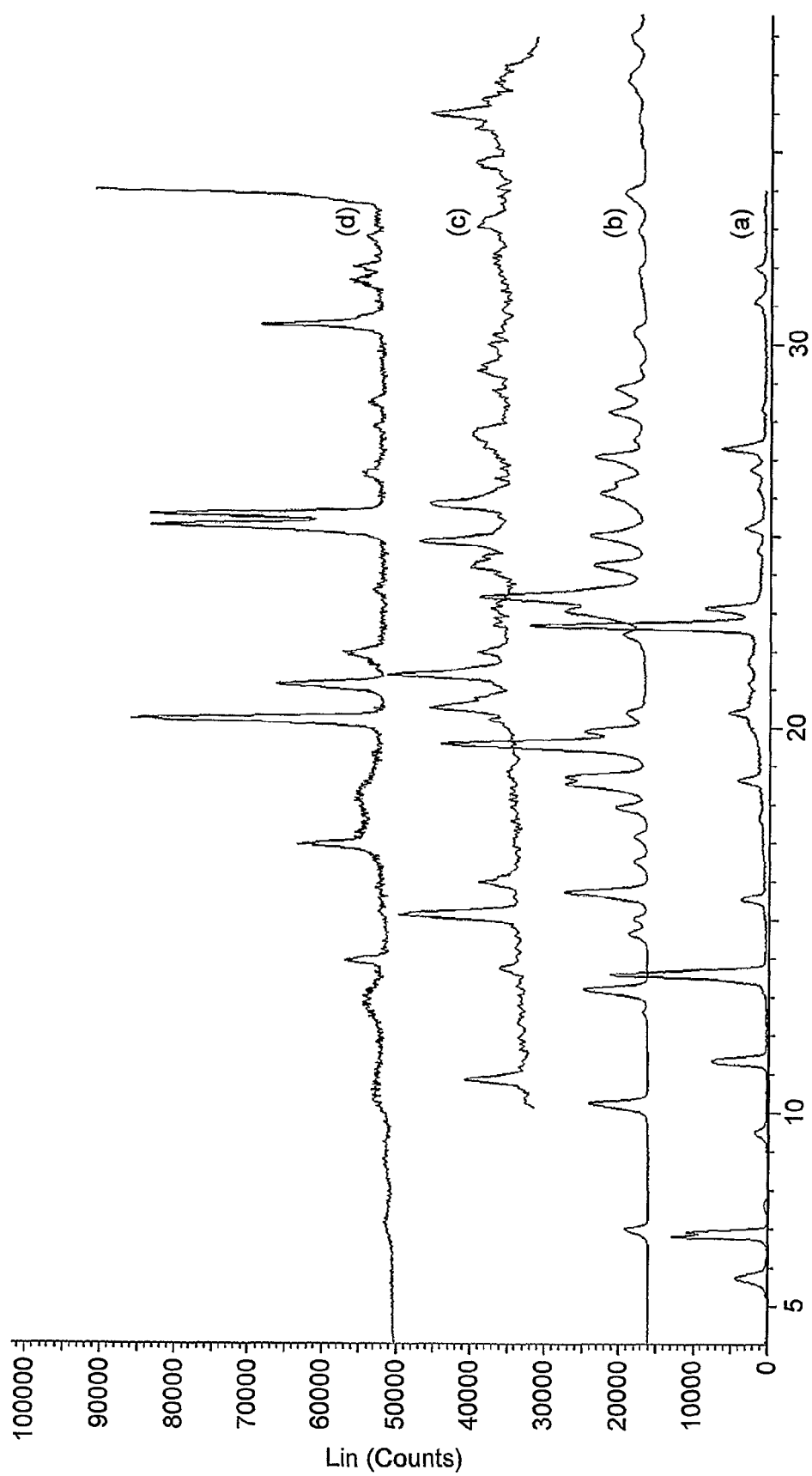
FIG. 23 shows Powder X-Ray Diffraction patterns of Cyprodinil Form A (a), Cyprodinil Form B (b), Cyprodinil-Glycolic acid Co-Crystal Form B (c) and Glycolic acid (d).

FIG. 23: Powder X-Ray Diffraction patterns of Cyprodinil Form A (a), Cyprodinil Form B (b), Cyprodinil-Glycolic acid Co-Crystal Form B (c) and Glycolic acid (d)

Table 15: 2θ values of selected peak positions of the Powder X-Ray Diffraction patterns of Cyprodinil-glycolic acid Co-Crystal.

TABLE 15

| Cyp-Glycolic Acid co-crystal |
|---|
| 2θ |
| 13.8 |
| 17.0 |
| 20.1 |
| 21.2 |
| 22.0 |
| 25.5 |
| 26.5 |
| 27.0 |
| 30.5 |
| 31.6 |
| 32.1 |

Experimental

For a 1:2 Co-Crystal by Cooling Crystallisation

100 µl of a 27.5% CYP in acetone solution was added to a well in 96 well plate.

168 µl of a 10% glycolic acid in methanol solution was added to this mixture with a further 50 µl of ethyl acetate. The sample was kept at 50° C. for 2 hours, then cooled to 10° C. overnight and the remaining liquid was removed.

Figure 24:
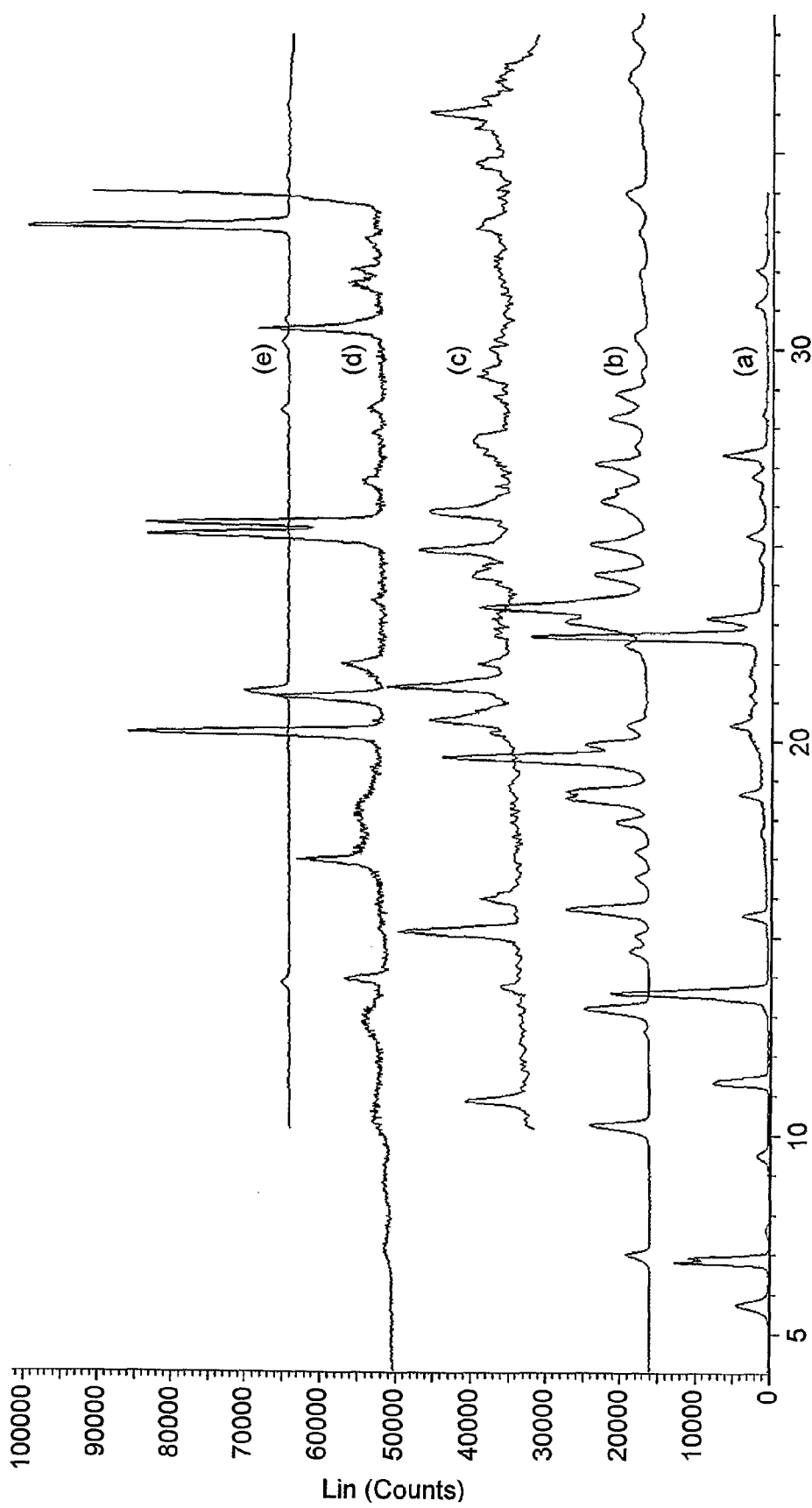
FIG. 24 shows Powder X-Ray Diffraction patterns of Cyprodinil Form A (a), Cyprodinil Form B (b), Cyprodinil-Glycolic acid Co-Crystal Form B (c), Glycolic acid (d) and Glycolic acid (e).

FIG. 24: Powder X-Ray Diffraction patterns of Cyprodinil Form A (a), Cyprodinil Form B (b), Cyprodinil-Glycolic acid Co-Crystal Form B (c), Glycolic acid (run on the D8) (d) and Glycolic acid (e)

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A co-crystal comprising cyprodinil and a co-crystal forming compound which has at least one organic acid functional group, wherein said co-crystal forming compound is:
   a) benzoic acid and the co-crystal is characterised by a powder X-ray diffraction pattern expressed in terms of 2 theta angles, wherein the powder X-ray diffraction pattern comprises the 2 theta angle values 11.201, 11.660, 13.978, 15.050, 18.584,19.297, 20.793, 23.865, 25.697, and 26.765; or
   b) succinic acid and the co-crystal is characterised by a powder X-ray diffraction pattern expressed in terms of 2 theta angles, wherein the powder X-ray diffraction pattern comprises the 2 theta angle values 12.5, 17.3, 18.7, 21.0, 22.4, 24.0, 25.4, 28.8 and 29.3; and wherein hydrogen-bonding occurs between the co-crystal forming compound and the cyprodinil.

2. The co-crystal of claim 1, wherein the co-crystal forming compound is succinic acid.

3. A process of preparing a co-crystal of claim 1 comprising
   a) grinding, heating or contacting in solution cyprodinil with the co-crystal forming compound, under crystallisation conditions so as to form a solid phase;

b) isolating co-crystals comprising cyprodinil and the co-crystal forming compound.

4. A fungicidal composition comprising the co-crystal of claim 1.

5. The composition of claim 4 which is an agrochemical composition.

6. A method of preventing/controlling fungal infection on plants comprising treating the plant with a fungicidally effective amount of an agricultural composition of claim 5.

\* \* \* \* \*